US009676855B2

(12) United States Patent
Cerwenka et al.

(10) Patent No.: US 9,676,855 B2
(45) Date of Patent: Jun. 13, 2017

(54) B7-H6 THERAPEUTICALLY ACTIVE MONOCLONAL ANTIBODY AGAINST B7-H6 POLYPEPTIDE

(75) Inventors: Adelheid Cerwenka, Heidelberg (DE); Gerhard Moldenhauer, Heidelberg (DE)

(73) Assignee: DEUTSCHES KREBSFORSCHUNGSZENTRUM, Heidelberg (DE)

( * ) Notice: Subject to any disclaimer, the term of this patent is extended or adjusted under 35 U.S.C. 154(b) by 447 days.

(21) Appl. No.: 14/344,499

(22) PCT Filed: Sep. 10, 2012

(86) PCT No.: PCT/EP2012/067637
§ 371 (c)(1),
(2), (4) Date: Jul. 14, 2014

(87) PCT Pub. No.: WO2013/037727
PCT Pub. Date: Mar. 21, 2013

(65) Prior Publication Data
US 2014/0341915 A1 Nov. 20, 2014

Related U.S. Application Data

(60) Provisional application No. 61/534,292, filed on Sep. 13, 2011.

(51) Int. Cl.
*C07K 16/28* (2006.01)
*G01N 33/53* (2006.01)
*G01N 33/574* (2006.01)
*G01N 33/68* (2006.01)

(52) U.S. Cl.
CPC ... *C07K 16/2827* (2013.01); *G01N 33/57492* (2013.01); *G01N 33/6854* (2013.01); *C07K 2317/76* (2013.01); *G01N 2333/70532* (2013.01); *G01N 2800/24* (2013.01)

(58) Field of Classification Search
None
See application file for complete search history.

(56) References Cited

U.S. PATENT DOCUMENTS

| 2011/0081346 A1 | 4/2011 | Brandt et al. | |
| 2013/0004432 A1* | 1/2013 | Pierres | C07K 16/2827 424/9.34 |
| 2015/0110760 A1* | 4/2015 | Zhang | C07K 14/70503 424/93.71 |

FOREIGN PATENT DOCUMENTS

| WO | WO 2009/046407 A2 | 4/2009 |
| WO | WO 2011/070443 A1 | 6/2011 |

OTHER PUBLICATIONS

Matta et al. (Blood 2013; 122(3): 394-404).*
Xu et al., Journal of Molecular Biology 2016, 428(22): 4457-4466.*
Jemal et al., "Cancer Statistics," *CA Cancer J. Clin.*, vol. 60, No. 5, pp. 277-300 (2010).
Vivier et al., "Functions of natural killer cells," *Nat. Immuno.*, vol. 9, No. 5, pp. 503-510 (2008).
Smyth et al., "New Aspects of Natural-Killer-Cell Surveillance and Therapy of Cancer," *Nat. Rev. Cancer*, vol. 2, pp. 850-861 (2002).
Lanier L.L., "NK Cell Recognition," *Ann. Rev. Immunol.*, vol. 23, pp. 225-274 (2005).
Parham P., "MHC Class I Molecules and KIRS in Human History, Health and Survival," *Nat. Rev. Immunol.*, vol. 5, pp. 201-204 (2005).
Pende et al., "Major Histocompatibility Complex Class I-related Chain A and UL16-Binding Protein Expression on Tumor Cell Lines of Different Histotypes: Analysis of Tumor Susceptibility to NKG2D-dependent Natural Killer Cell Cylotoxicity," *Cancer Res.*, vol. 62, pp. 6178-6186 (2002).
Moretta et al., "Activating Receptors and Coreceptors Involved in Human Natural Killer Cell-Mediated Cytolysis," *Annu. Rev. Immunol.*, vol. 19, pp. 197-223 (2001).
Brandt et al., "The B7 family member B7-H6 is a tumor cell ligand for the activating natural killer cell receptor NKp30 in humans," *J. Exp. Med.*, vol. 206, No. 7, pp. 1495-1503 (2009).
Giudicelli et al., "Ontology for immunogenetics: the IMGT-Ontology," *Bioinformatics*, vol. 15, No. 2, pp. 1047-1054 (1999).
Ewert et al., "Stability improvement of antibodies for extracellular and intracellular applications: CDR grafting to stable frameworks and structure-based framework engineering," *Methods*, vol. 34, No. 2, pp. 184-199 (2004).
Lo B.K.C., "Antibody Humanization by CDR Grafting," *Methods in Molecular Biology*, vol. 248, II, pp. 135-159 (2004).
Arnon et al., "Monoclonal Antibodies for Immunotargeting of Drugs in Cancer Therapy," *Monoclonal Antibodies and Cancer Therapy*, pp. 243-256 (1985).
Li et al., "Structure of the human activating natural cytotoxicity receptor NKp30 bound to its tumor cell ligand B7-H6," *J. Exper. Med.*, vol. 208, No. 4, pp. 703-714 (2011).
Joyce et al., "Crystal structure of human natural cytotoxicity receptor NKp30 and identification of its ligand binding site," *PNAS*, vol. 108, No. 15, pp. 6223-6228 (2011).
Seliger et al., "The expression, function, and clinical relevance of B7 family members in cancer," *Cancer Immunol. Immunother.*, vol. 61, No. 8, pp. 1327-1341 (2012).
Flajnik et al., "Evolution of the B7 family: co-evolution of B7H6 and NKp30, identification of a new B7 family member, B7H7, and of B7's historical relationship with the MHC," *Immunogenetics*, vol. 64, No. 8, pp. 571-590 (2012).

(Continued)

*Primary Examiner* — Ilia Ouspenski
(74) *Attorney, Agent, or Firm* — Foley & Lardner LLP

(57) ABSTRACT

The present invention is concerned with diagnostic methods and means. Specifically, it relates to an antibody which specifically binds to a portion of the extracellular domain of the B7-H6 polypeptide. Moreover, said antibody is provided for use in the treatment or diagnosis of cancer or inflammatory disease. Furthermore, provided are a method for diagnosing cancer in a sample of a subject suspected to suffer from cancer or an inflammatory disease. Further, the present invention concerns a device and a kit for diagnosing cancer or an inflammatory.

8 Claims, 12 Drawing Sheets

(56) References Cited

OTHER PUBLICATIONS

Abcam: "Anti-B7-H6 antibody (ab121794) Datasheet," scimall.cn, Jul. 18, 2012, retrieved from the Internet: URL:http://www.scimall.cn/images/u120714/abcam5/B7-H6-antibody-ab121794.pdf (retrieved on Nov. 9, 2013), 2 pages.

International Preliminary Report on Patentability issued in related International Patent Application No. PCT/EP2012/067637, dated Mar. 27, 2014.

International Search Report issued in related International Patent Application No. PCT/EP2012/067637, completed Nov. 12, 2012.

* cited by examiner

```
Signal    1 M  E  Q  R  G  Q  N  A  P  A  A  S  G  A  R  K  R  H  G  P
Peptid    1 ATGGAACAACGGGGACAGAACGCCCCGGCCGCTTCGGGGGCCCGGAAAAGGCACGGCCCA
         21 G  P  R  E  A  R  G  A  R  P  G  P  R  V  P  K  T  L  V  L
         61 GGACCCAGGGAGGCGCGGGGAGCCAGGCCTGGGCCCCGGGTCCCCAAGACCCTTGTGCTC
                                                             BamHI
         41 V  V  A  A  V  L  L  L  V  S  A  E  S  A  L  E  S  D  L  K
        121 GTTGTCGCCGCGGTCCTGCTGTTGGTCTCAGCTGAGTCTGCTCTGGAATCCGATCTGAAA
         61 V  E  M  M  A  G  G  T  Q  I  T  P  L  N  D  N  V  T  I  F
        181 GTAGAGATGATGGCAGGGGGGACTCAGATCACACCCCTGAATGACAATGTCACCATATTC
B7-H6    81 C  N  I  F  Y  S  Q  P  L  N  I  T  S  M  G  I  T  W  F  W
        241 TGCAATATCTTTTATTCCCAACCCCTCAACATCACGTCTATGGGTATCACCTGGTTTTGG
        101 K  S  L  T  F  D  K  E  V  K  V  F  E  F  F  G  D  H  Q  E
        301 AAGAGTCTGACGTTTGACAAAGAAGTCAAAGTCTTTGAATTTTTTGGAGATCACCAAGAG
        121 A  F  R  P  G  A  I  V  S  P  W  R  L  K  S  G  D  A  S  L
        361 GCATTCCGACCTGGAGCCATTGTGTCTCCATGGAGGCTGAAGAGTGGGGACGCCTCACTG
        141 R  L  P  G  I  Q  L  E  E  A  G  E  Y  R  C  E  V  V  V  T
        421 CGGCTGCCTGGAATCCAGCTGGAGGAAGCAGGAGAGTACCGATGTGAGGTGGTGGTCACC
        161 P  L  K  A  Q  G  T  V  Q  L  E  V  V  A  S  P  A  S  R  L
        481 CCTCTGAAGGCACAGGGAACAGTCCAGCTTGAAGTTGTGGCTTCCCCAGCCAGCAGATTG
        181 L  L  D  Q  V  G  M  K  E  N  E  D  K  Y  M  C  E  S  S  G
        541 TTGCTGGATCAAGTGGGCATGAAAGAGAATGAAGACAAATATATGTGTGAGTCAAGTGGG
        201 F  Y  P  E  A  I  N  I  T  W  E  K  Q  T  Q  K  F  P  H  P
        601 TTCTACCCAGAGGCTATTAATATAACATGGGAGAAGCAGACCCAGAAGTTTCCCCATCCC
        221 I  E  I  S  E  D  V  I  T  G  P  T  I  K  N  M  D  G  T  F
        661 ATAGAGATTTCTGAGGATGTCATCACTGGTCCCACCATCAAGAATATGGATGGCACATTT
        241 N  V  T  S  C  L  K  L  N  S  S  Q  E  D  P  G  T  V  Y  Q
        721 AATGTCACTAGCTGCTTGAAGCTGAACTCCTCTCAGGAAGACCCTGGGACTGTCTACCAG
        261 C  V  V  R  H  A  S  L  H  T  P  L  R  S  N  F  T  L  T  A
        781 TGTGTGGTACGGCATGCGTCCTTGCATACCCCCTTGAGGAGCAACTTTACCCTGACTGCT
        281 A  R  H  S  L  S  E  T  E  K  T  D  N  F  S  I  H  W  W  P
        841 GCTCGGCACAGTCTTTCTGAAACTGAGAAGACAGATAATTTTTCCATTCATTGGTGGCCT
            EcoRV
        301 D  I  T  H  T  C  P  P  C  P  A  P  E  A  E  G  A  P  S  V
        901 GATATCACTCACACATGCCCACCGTGCCCAGCACCTGAAGCCGAGGGCGCGCCGTCAGTC
        321 F  L  F  P  P  K  P  K  D  T  L  M  I  S  R  T  P  E  V  T
Fcm     961 TTCCTCTTCCCCCCAAAACCCAAGGACACCCTCATGATCTCCCGGACCCCTGAGGTCACA
        341 C  V  V  V  D  V  S  H  E  D  P  E  V  K  F  N  W  Y  V  D
       1021 TGCGTGGTGGTGGACGTGAGCCACGAAGACCCTGAGGTCAAGTTCAACTGGTACGTGGAC
        361 G  V  E  V  H  N  A  K  T  K  P  R  E  E  Q  Y  N  S  T  Y
       1081 GGCGTGGAGGTGCATAATGCCAAGACAAAGCCGCGGGAGGAGCAGTACAACAGCACGTAC
        381 R  V  V  S  V  L  T  V  L  H  Q  D  W  L  N  G  K  E  Y  K
       1141 CGTGTGGTCAGCGTCCTCACCGTCCTGCACCAGGACTGGCTGAATGGCAAGGAGTACAAG
        401 C  K  V  S  N  K  A  L  P  A  P  I  E  K  T  I  S  K  A  K
       1201 TGCAAGGTCTCCAACAAAGCCCTCCCAGCCCCCATCGAGAAAACCATCTCCAAAGCCAAA
        421 G  Q  P  R  E  P  Q  V  Y  T  L  P  P  S  R  E  E  M  T  K
       1261 GGGCAGCCCCGAGAACCACAGGTGTACACCCTGCCCCCATCCCGGGAGGAGATGACCAAG
        441 N  Q  V  S  L  Q  P  E  N  N  Y  K  T  T  P  P  V  L  D  S
       1321 AACCAGGTCAGCCTGCAGCCGGAGAACAACTACAAGACCACGCCTCCCGTGCTGGACTCC
```

Fig. 1

```
      461 D  G  S  F  F  L  Y  S  K  L  T  V  D  K  S  R  W  Q  Q  G
     1381 GACGGCTCCTTCTTCCTCTATAGCAAGCTCACCGTGGACAAGAGCAGGTGGCAGCAGGGG
      481 N  V  F  S  C  S  V  M  H  E  A  L  H  N  H  Y  T  Q  K  S
     1441 AACGTCTTCTCATGCTCCGTGATGCATGAGGCTCTGCACAACCACTACACGCAGAAGAGC
                                             NdeI
      501 L  S  L  S  P  G  K  H  M  G  G  D  E  K  T  T  G  W  R  G
     1501 CTCTCCCTGTCTCCGGGTAAACATATGGGAGGTGACGAAAAGACCACCGGCTGGCGCGGC
SBP   521 G  H  V  V  E  G  L  A  G  E  L  E  Q  L  R  A  R  L  E  H
     1561 GGCCACGTGGTGGAAGGCCTGGCCGGCGAACTGGAACAGCTGCGCGCCCGCCTGGAACAC
                                                       XhoI
      541 H  P  Q  G  Q  R  E  P  *  L  E
     1621 CACCCACAGGGCCAGCGCGAACCATGACTCGAG
```

Fig. 1 (continued)

1 DLKVEMMAGGTQITPLNDNVTIFCNIFYSQPLNITSMGITWFWKSLTFDKEVKVFEFFGD
    ─────────────────────────────────────────────────────────────
                              IgV-like domain
 61 HQEAFRPGAIVSPWRLKSGDASLRLPGIQLEEAGEYRCEVVVTPLKAQGTVQLEVVASPA
    ─────────────────────────────────────────────────────────  ══

121 SRLLLDQVGMKENEDKYMCESSGFYPEAINITWEKQTQKFPHPIEISEDVITGPTIKNMD
    ════════════════════════════════════════════════════════════
                              IgC-like domain
181 GTFNVTSCLKLNSSQEDPGTVYQCVVRHASLHTPLRSNFTLTAARHSLSETEKTDNFSIH
    ════════════════════════════════════════════════════════════

241 WWP

Fig. 2

B7-H6_1 (amino acids 24-454)
B7-H6_2 (amino acids 83-454)
B7-H6_3 (amino acids 141-454)
B7-H6_4 (amino acids 190-454)
B7-H6_5 (amino acids 239-454)

B7-H6 THERAPEUTICALLY ACTIVE MONOCLONAL ANTIBODY AGAINST B7-H6 POLYPEPTIDE

This application is the National Phase of PCT/EP2012/067637, filed on Sep. 10, 2012, which claims priority to U.S. Provisional Patent Application No. 61/534,292, filed Sep. 13, 2011. The contents of these applications are incorporated herein by reference in their entirety.

The present invention is concerned with diagnostic methods and means. Specifically, it relates to an antibody which specifically binds to a portion of the extracellular domain of the B7-H6 polypeptide. Moreover, said antibody is provided for use in the treatment or diagnosis of cancer or inflammatory disease. Furthermore, provided are a method for diagnosing cancer in a sample of a subject suspected to suffer from cancer or an inflammatory disease. Further, the present invention concerns a device and a kit for diagnosing cancer or inflammation.

BACKGROUND

Until today, cancer is one of the leading causes of deaths in the United States, even though progress has been made in reducing incidence and mortality rates and improving survival (see Jemal et al. 2010, CA Cancer J Clin. September-October 60(5):277-300). Further progress can be accelerated by improving diagnostic methods and means due to the fact that cancer development is often associated with the lack of specific recognition of tumor cells by the immune system.

Targeted cancer therapy comprises medication which interferes with specific targeted molecules (e.g., monoclonal or polyclonal antibodies) to directly block the growth of cancer cell. Thus, targeted cancer therapy may be more effective than traditional therapeutic approaches (e.g., resection, radiation, chemotherapy) and may be less harmful to normal cells. Monoclonal antibodies (mAb) can be designed to specifically bind to an extracellular domain or to a cell surface target of the target cell to stimulate the immune system of the patient. Monoclonal antibodies can also be created for numerous serious diseases (e.g., inflammatory diseases or different types of cancers). Thus, monoclonal antibodies may provide reliable and efficient therapeutic and diagnostic methods and means to e.g., detect early developmental stages of these diseases or to offer therapeutic approaches.

Natural killer cells (NK cells) constitute a major component of the innate immune system shaping the inflammatory and adaptive immune response (see Vivier et al. 2008, Nat. Immuno. 9:503-510) and playing a crucial role in the rejection of transformed and virally infected cells (see Smyth et al. 2002, Nat. Rev. Cancer 2:850-861; Lanier 2005, Annu Rev. Immunol. 23:225-274). NK cells survey target cells for expression of major histocompatibility complex (MHC) class I (see Parham 2005, Nat. Rev. Immunol. 5:201-204) which protects the target cell from NK cell activation and from NK cell attack. Target cells which lack MHC class I are directly killed by NK cells due to the induction of apoptosis (programmed cell death). The discovery of NK-activating receptors (e.g., the natural cytotoxicity receptor (NCR) family like NKp30) revealed that also activation signals are necessary for the activation of NK cells and tumor cell lysis (see Pende et al. 1999, Cancer Res. 62:6178-6186; Moretta et al. 2001, Annu Rev. Immunol. 19:197-223).

Recently, it could be shown that the human NKp30 directly interacts with the B7 family member B7-H6 whose expression on tumor cells induces NKp30-dependent cell activation and cytotoxity (see Brandt et al. 2009, J. Exp. Med. 206(7):1495-1503; US 2011/0081346). Hereby, the extracellular domain of NKp30 directly interacts with the extracellular domain of B7-H6 which is exclusively expressed on the surface of several tumor cell lines (see Brandt et al. 2009, J. Exp. Med. 206(7):1495-1503).

SUMMARY OF THE INVENTION

The present invention relates to an antibody which specifically binds to an epitope formed by a portion of the extracellular domain of the B7-H6 polypeptide, said portion having an amino acid sequence as shown in SEQ ID NO: 22. Preferably, said sequence represents an IgV-like domain.

In a preferred embodiment of the antibody of the invention, said antibody comprises complementarity determining regions (CDRs) as shown in SEQ ID NOs: 5, 7, 9, 15, 17, and 19. Nucleic acid sequences of the above mentioned CDRs were annotated according to the IMGT-ONTOLOGY (see Giudicelli and Lefranc 1999, Bioinformatics 15:1047-1054).

In a preferred embodiment of the antibody of the invention, said antibody is a monoclonal antibody. More preferably, said antibody is the antibody deposited under accession number DSM ACC 3117 at the DSMZ, Braunschweig, Germany under the Budapest treaty on Feb. 2, 2011.

The present invention contemplates an antibody of the invention for use in the treatment or diagnosis of cancer. Preferably, the cancer is T cell lymphoma, myeloid leukemia, colon carcinoma, B cell lymphoma, melanoma, or cervical carcinoma.

The present invention, furthermore, contemplates an antibody of the invention for use in the treatment or diagnosis of inflammatory disease. Preferably, the inflammatory disease is a viral infection.

The present invention relates to a method for diagnosing cancer in a sample of a subject suspected to suffer from cancer comprising:
a) contacting the sample with the antibody of the invention under conditions which allow for binding of said antibody to its epitope on the B7-H6 polypeptide; and
b) determining binding of the antibody to the said epitope, whereby cancer is diagnosed.

In a preferred embodiment of the method of the invention, the cancer is T cell lymphoma, myeloid leukemia, colon carcinoma, B cell lymphoma, melanoma, or cervical carcinoma.

The present invention also relates to a method for diagnosing an inflammatory disease in a sample of a subject suspected to suffer from an inflammatory disease comprising:
a) contacting the sample with the antibody of the invention under conditions which allow for binding of said antibody to its epitope on the B7-H6 polypeptide; and
b) determining binding of the antibody to the said epitope, whereby the inflammatory disease is diagnosed.

In a preferred embodiment of the method of the invention, said sample is a tissue or body fluid sample.

Encompassed by the invention is also a device for diagnosing cancer or an inflammatory disease in a sample comprising:
a) an analyzing unit comprising the antibody of the invention; and
b) a detector which detects binding of the antibody in the analyzing unit to its epitope on the B7-H6 polypeptide.

In a preferred embodiment of the device of the invention, said sample is a tissue or body fluid sample.

The present invention finally relates to a kit for diagnosing cancer or an inflammatory disease comprising the antibody of the invention and, preferably, an agent for detection of binding of said antibody to its epitope on the B7-H6 polypeptide.

FIGURES

FIG. 1 shows the nucleic acid and amino acid sequences of the B7-H6-Ig-fusionprotein. Italic nucleic acid and amino acid sequences indicate enzymatic restriction sites. Nucleic acid and amino acid sequences of the extracellular domain of human B7-H6 are underlined bold, whereby said sequences of Fcm are dotted underlined.

FIG. 2 shows the amino acid sequence of the extracellular domain of the human B7-H6 polypeptide and indicates the IgV-like domain and the IgC-like domain.

Figure 6A:
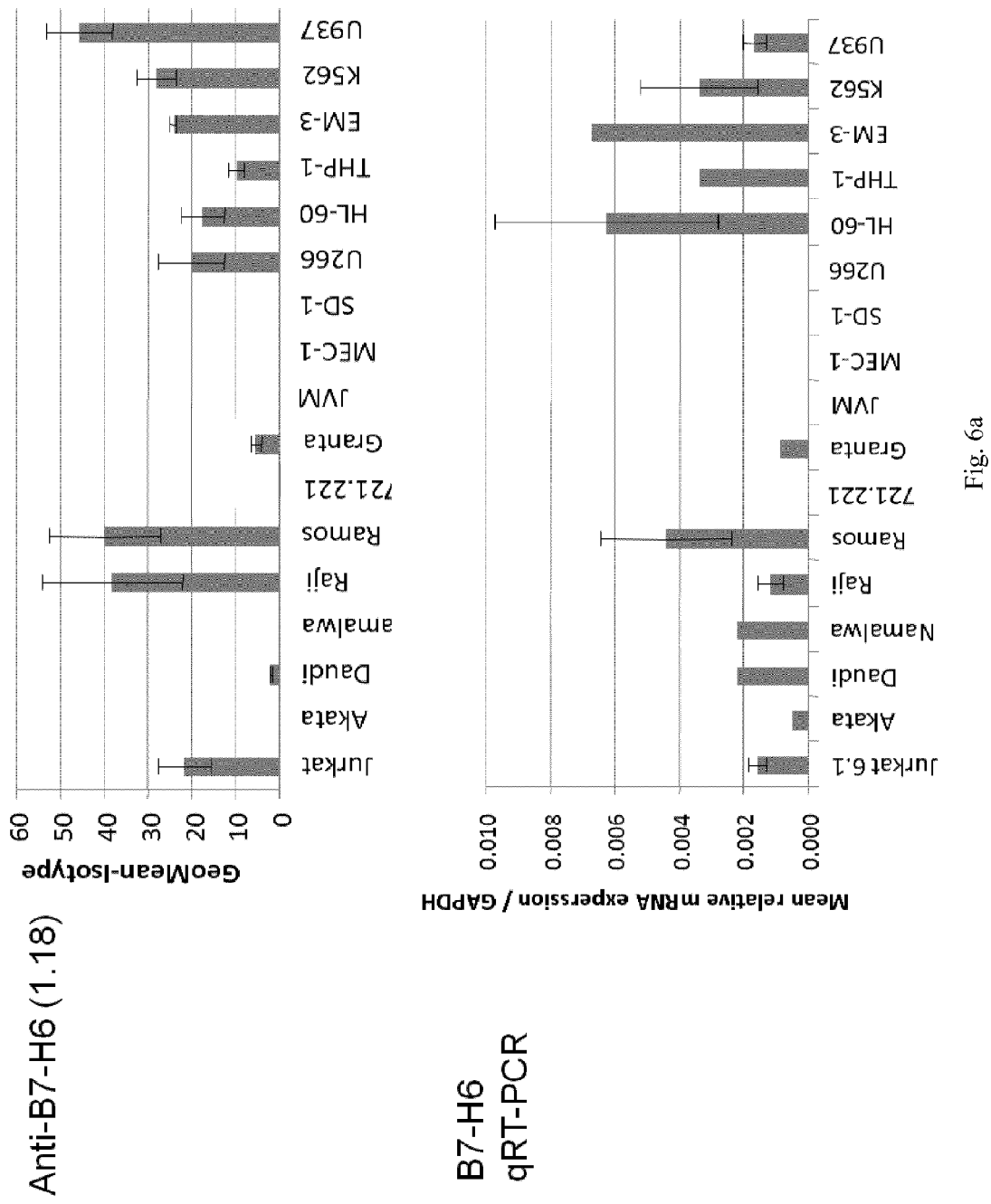
Figure 6B:
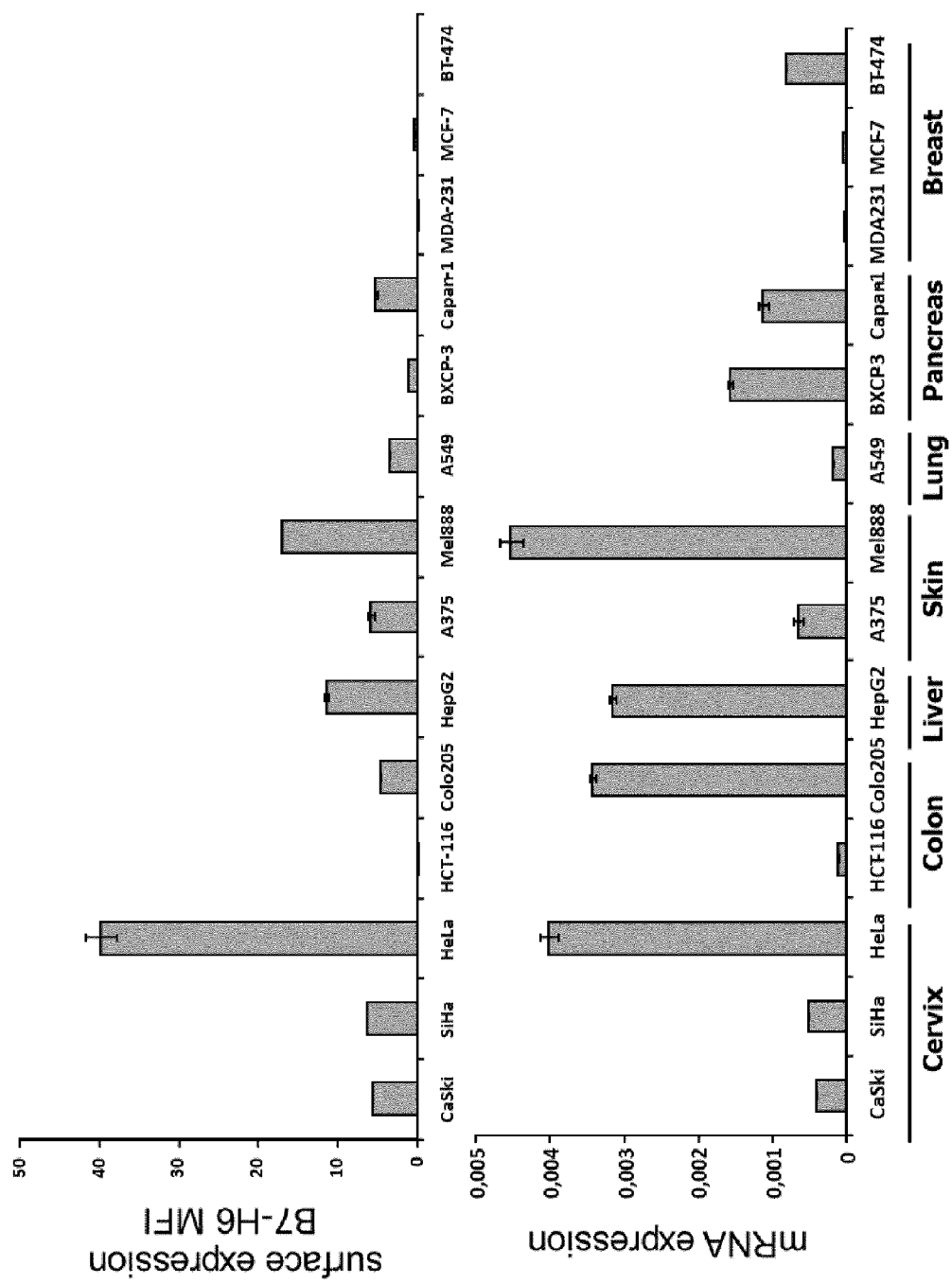

FIG. 6 depicts that cell surface expression of B7-H6 determined by fluorescence-activated cell sorting (FACS) and mRNA expression in the different cell lines. FIG. 6a shows the expression of B7-H6 in tumor cell lines of hematopoietic origin. FIG. 6b shows the expression of B7-H6 in tumor cell lines of solid tumor origin.

Figure 7:
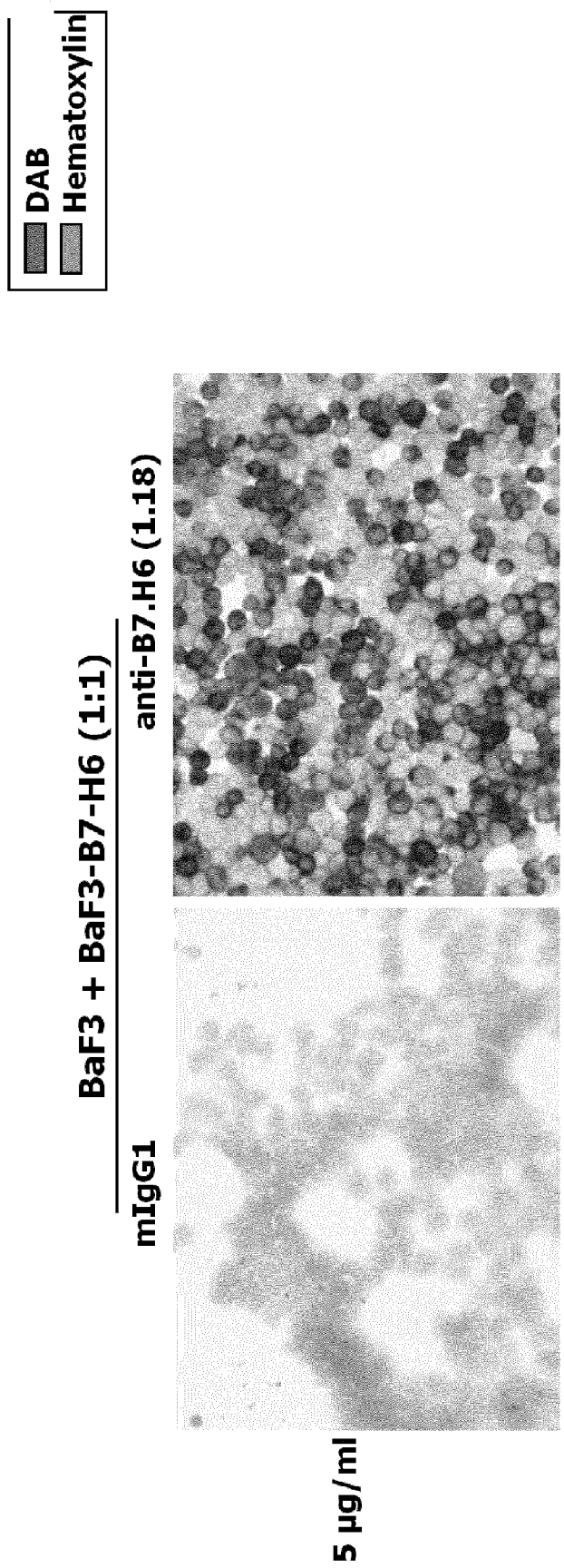

FIG. 7 shows that the anti-B7-H6 mAb 1.18 detects B7-H6 on cytospins (frozen sections) of BA/F-3-B7-H6 transfectants.

Figure 8:
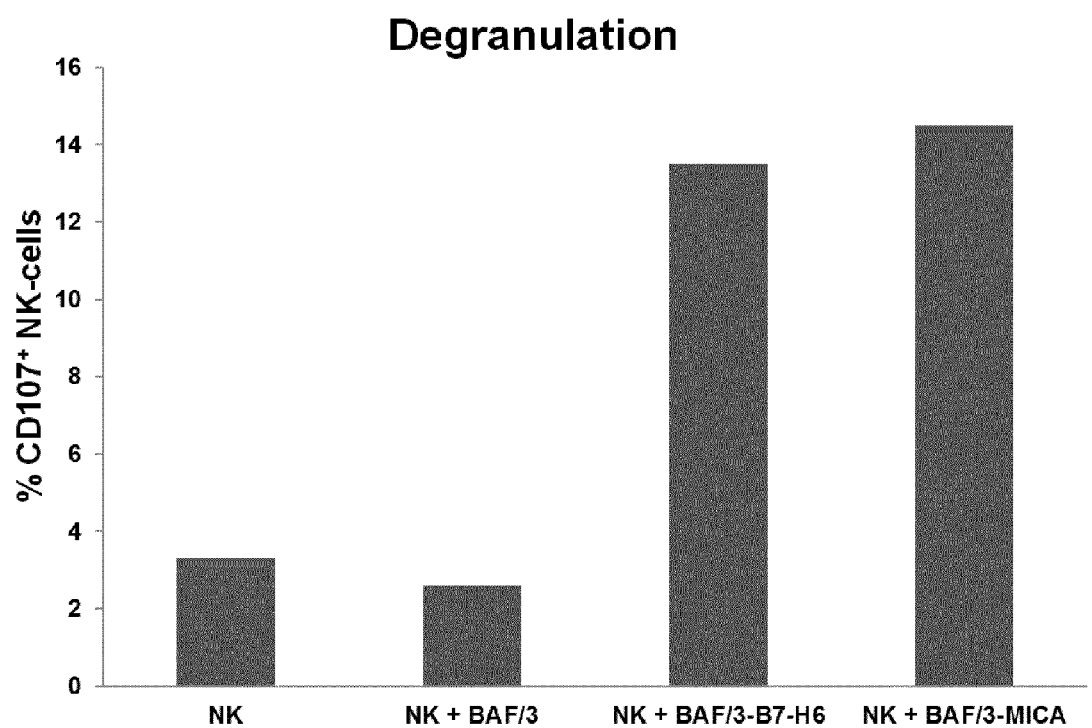

FIG. 8 shows that primary natural killer (NK) cells degranulate upon co-culture with BA/F3-B7-H6 transfectants.

DETAILED DESCRIPTION OF THE INVENTION

The present invention relates to an antibody which specifically binds to an epitope formed by a portion of the extracellular domain of the B7-H6 polypeptide, said portion having an amino acid sequence as shown in SEQ ID NO: 22. Preferably, said sequence represents an IgV-like domain.

The term "antibody" refers to all types of antibodies which specifically bind to an epitope comprised in a portion of the extracellular domain of the B7-H6 polypeptide. Epitopes as referred to herein are, preferably, defined by stretches of 7 to 15, preferably 8 to 11 contiguous amino acids in length. However, an epitope in accordance with the present invention can also be formed by a certain three-dimensional structure and such structural epitopes are also envisaged herein. Specific binding in this context means that the antibody of the invention essentially binds to the epitope without significant cross-reactivity (i.e. binding) to other epitopes either on the B7-H6 polypeptide or other polypeptides. Specific binding can be determined by techniques well known in the art. Preferably, the antibody binds specifically to the said epitope. The aforementioned epitope shall be located in a portion of the extracellular domain of the B7-H6 polypeptide. Preferably, the B7-H6 polypeptide has an amino acid sequence as shown in SEQ ID NO: 2 and the said extracellular domain corresponds to amino acids 58 to 300 of said sequence (see also FIGS. 1 and 2). It will be understood that the B7-H6 polypeptide may also be represented by a variant sequence of SEQ ID NO: 2 which differs therefrom by substitution, addition and/or deletion of one or more amino acids. Such variant sequences may be orthologous amino acid sequences from other species as well as paralogous or other homologous sequences of the aforementioned specific B7-H6. Preferably, such variant sequences are at least 70%, at least 80%, at least 90%, at least 95% or at least 99% identical over the entire length or at least 50% of SEQ ID NO: 2 with the said sequence. The term "sequence identity" as used herein refers to a relationship between two or more polypeptide sequence, namely a reference sequence and a given sequence to be compared with the reference sequence. Sequence identity can be determined by comparing the given sequence to the reference sequence after the sequences have been aligned optimally to produce the highest degree of sequence similarity which can be determined by the match between strings of such sequences. Said alignment can be performed by a skilled artisan without further ado. Accordingly, sequence identity provides information on the total number of said matches.

Sequence identity can be, preferably, calculated using publicly available computer programs which are known by a skilled artisan, e.g., BLAST and FASTA. Other sequence variants envisaged in accordance with the present invention are those which are encoded by nucleic acid molecules capable of hybridizing under stringent hybridization conditions to the nucleic acid sequence encoding B7-H6 shown in SEQ ID NO: 1. Preferably, the B7-H6 polypeptide is encoded by the nucleic acid sequence shown in SEQ ID NO: 1. Stringent hybridization conditions referred to in accordance with the present invention are equivalent to hybridization in 7% sodium dodecyl sulfate (SDS), 0.5 M NaPO4, 1 mM EDTA at 50° C. with washing in 1× SSC, 0.1% SDS at 50° C. or 65° C., wherein nucleic acid molecule probe comprising at least 100, more preferably at least 150, even more preferably at least 200, most preferably at least 250 consecutive nucleotides of SEQ ID NO:1 or its reverse complement is used. It will be understood that the first and the last amino acid of the extracellular domain in such sequence variants may differ from the positions indicated for SEQ ID NO: 2, above. However, the extracellular domain will start and end at positions corresponding to the said positions. Such corresponding positions can be determined by sequence analysis tools by the skilled artisan without further ado.

Preferably, an antibody as referred to in accordance with the present invention encompasses a monoclonal antibody, a single chain antibody, a chimeric antibody or any fragment or derivative of such antibodies having the above mentioned binding properties. Such fragments and derivatives comprised by the term antibody as used herein encompass a synthetic antibody, an Fab, F(ab)$_2$ Fv or scFv fragment, or a chemically modified derivative of any of these antibodies. Chemical modifications envisaged preferably by the present invention include those which aim to couple the antibody to a detectable marker as specified elsewhere in this specification. Antibodies or fragments thereof, in general, can be obtained by using methods which are described, e.g., in Harlow and Lane "Antibodies, A Laboratory Manual", CSH Press, Cold Spring Harbor, 1988.

Advantageously, the antibody of the present invention specifically binds to B7-H6 with a high affinity. In the studies underlying the present invention it has been found that compared to other anti-B7-H6 antibodies described or suggested in the prior art (Brandt 2009, J. Exp. Med. 206(7): 1495-1503 and US 2011/0081346), the antibody is particularly useful in in vivo applications such as FACS sorting and cell culture as well as in vitro applications including immunohistochemistry on, e.g., frozen tissue sections. Thanks to the present invention, cancer diagnosis based on the determination of B7-H6 will improve. Moreover, therapeutic approaches which aim to target anti-tumor drugs to B7-H6 positive cells are feasible.

In a preferred embodiment of the antibody of the present invention, said antibody comprises complementarity determining regions (CDRs) as shown in SEQ ID NOs: 5, 7, 9, 15, 17, and 19. Nucleic acid sequences of the above mentioned CDRs were annotated according to the IMGT-ONTOLOGY (see Giudicelli and Lefranc 1999, Bioinformatics 15:1047-1054).

The term "complementarity determining region" or "CDR" as used herein refers to variable domains of an antibody which are responsible for the specificity in antigen binding. An antigen, usually, comprises three CDRs (CDR1, CDR2 and CDR3). These CDRs are arranged in a non-consecutive manner. Since the antigen recognizing portions of the antibody are typically composed of two variable domains on a heavy and a light chain, six CDRs come into contact with the antigen upon binding. The CDRs can be transferred from one antibody species to another by conventional molecular biology techniques such as CDR grafting (see Ewert 2004, Methods 34(2): 184-199; Benny K. C. Lo in Antibody Engineering—Methods in Molecular Biology 2004, Volume 248, II, 135-159, DOI 10.1385/1-59259-666-5:135).

It will be understood from the above that in another preferred embodiment, the antibody of the present invention is a monoclonal antibody.

Preferably, such a monoclonal antibody can be prepared by applying an immunogenic polypeptide having the portion of the extracellular domain as characterized above to a mammal, preferably a mouse. More preferably, the immunogenic polypeptide is conjugated to a carrier protein, such as bovine serum albumin, thyroglobulin, and keyhole limpet hemocyanin (KLH). Depending on the host species, various adjuvants can be used to increase the immunological response. Such adjuvants encompass, preferably, Freund's adjuvant, mineral gels, e.g., aluminum hydroxide, and surface active substances, e.g., lysolecithin, pluronic polyols, polyanions, peptides, oil emulsions, keyhole limpet hemocyanin, and dinitrophenol. Monoclonal antibodies according to the invention can be subsequently prepared using the well known hybridoma technique, the human B cell hybridoma technique, and the EBV hybridoma technique. Further details on the preparation of an antibody of the invention are described in the accompanying Examples below.

In a more preferred embodiment of the antibody of the present invention, the antibody is the antibody or the antibody produced by the corresponding hybridoma cell clone as deposited under accession number DSM ACC 3117 at the "DSMZ—Deutsche Sammlung von Mikroorganismen and Zellkulturen GmbH", 38124 Braunschweig, GERMANY on Feb. 2, 2011 according to the Budapest Treaty by "Deutsches Krebsforschungszentrum", Heidelberg, GERMANY.

The aforementioned anti-B7-H6 mAb shall comprise at least one heavy chain and at least one light chain. Preferably, anti-B7-H6 mAb has an amino acid sequence of the heavy chain (IGHV/IGHD/IGHJ) as shown in SEQ ID NO: 3, whereby the secreted form (IGHV/IGHD/IGHJ/IGHG1) is shown in SEQ ID NO: 11 and the membrane bound form (IGHV/IGHD/IGHJ/IGHG1) is shown in SEQ ID NO: 12. The nucleic acid sequences of fragments 1-4 of the heavy chain are shown in SEQ ID NO: 4, 6, 8, and 10 and the nucleic acid sequences of CDRs 1-3 of the heavy chain are shown in SEQ ID NO: 5, 7, and 9. Further, said antibody has an amino acid sequence of the light chain (IGLV/IGLJ) as shown in SEQ ID NO: 13, whereby the sequence of IGLV/IGLJ/IGLC is shown in SEQ ID NO: 21. The nucleic acid sequences of fragments 1-4 of the light chain are shown in SEQ ID NO: 14, 16, 18, and 20 and the nucleic acid sequences of CDRs 1-3 of the light chain are shown in SEQ ID NO: 15, 17, and 19. It will be understood that the anti-B7-H6 mAb may also be represented by variant sequences of the aforementioned SEQ ID NOs: 3-21 which differ therefrom by substitution, addition and/or deletion of one or more amino acids. Such variant sequences may be orthologous amino acid sequences from other species as well as paralogous or other homologous sequences of the aforementioned specific anti-B7-H6 mAb. Preferably, such variant sequences are at least 70%, at least 80%, at least 90%, at least 95% or at least 99% identical over the entire length or at least 50% of SEQ ID NOs: 3-21 with said sequences. The term sequence identity has been defined elsewhere in this description and applies mutatis mutandis.

The present invention further relates to an antibody of the invention for use in the treatment or diagnosis of cancer.

The term "treatment" as used herein encompasses the amelioration of a disease referred to herein or its symptoms as well as curing the disease, i.e. the reestablishment of the healthy condition in a subject with respect to the disease or its symptoms. Amelioration as referred to herein refers to a significant improvement of the health condition with respect to the disease or a symptom of the disease. Such a significant improvement is, preferably, clinically apparent in, e.g., staging or grading systems applied in order to investigate a subject. As will be understood by those skilled in the art, treatment as used herein is usually not intended to be correct for all (i.e. 100%) of the subjects under a given treatment. The term, however, requires that a statistically significant portion of subjects can be treated (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983.

Preferably, the antibody of the invention for use in treating cancer is either coupled to a cytotoxic agent or an anti-tumor agent or is capable of recruiting such agents suitable for treating cancer. The term "agent" as used herein refers to an element, compound, or other molecular entity (e.g., a pharmaceutical compound, a therapeutic compound, or a pharmacologic compound). Such an agent can be natural, synthetic or a combination thereof. The term "therapeutic agent" as used herein refers to an agent that either alone or in combination with another agent exhibits a therapeutic or beneficial effect on a cell or a tissue. Preferably, a therapeutic agent in accordance with the present invention shall comprise drugs, toxins, immunomodulators, chelators, boron compounds, photoactive agents or dyes, and radioisotopes. Techniques for coupling therapeutic agents to polypeptides such as to antibodies are well-known by the skilled artisan (e.g., Amon et al. 1985, "Monoclonal Antibodies For Immunotargeting Of Drugs In Cancer Therapy," in Monoclonal Antibodies And Cancer Therapy (Reisfeld et al. eds., Alan R. Liss, Inc., 1985)). The term "cytotoxic agent" as used herein refers to an agent that has a cytotoxic or cytostatic effect on a cell, thereby depleting or inhibiting the growth of, respectively, cells within a cell population. Preferably, cytotoxic agents in accordance with the present invention shall comprise anti-tubulin agents (e.g., dolastatins, vinca alkaloids, podophyllatoxins, taxanes, baccatin derivatives, cryptophysins, maytansinoids, and combretastatins), DNA minor groove binding agents, DNA replication inhibitors, alkylating agents (e.g., platinum complexes), anthracyclines, antibiotics, antifolates, antimetabolites, chemotherapy sensitizers, duocarmycins, etoposides, fluorinated pyrimidines, ionophores, lexitropsins, nitro soureas, platinols, pre-forming compounds, purine antimetabolites, puromycins, radiation sensitizers, steroids, taxanes, topoisomerase inhibitors, vinca alkaloids, or the like. The term "anti-tumor agent" as used herein refers to an agent that has a cytotoxic or malign effect on cancer cells, thereby arresting the growth of, respectively, cancer cells within a tumor resulting, preferably, in cell death. Preferably, the antibody of the invention binds to a target cell (e.g., a cancer cell) and specific effector cells expressing receptors for said antibody (e.g., natural killer cells, monocytes, granulocytes) which results in target cell death. In another preferred embodiment of the invention the antibody of the invention is coupled to a cytotoxic agent or an anti-tumor agent via a linker. Preferably, a linker in accordance with the present invention shall comprise linker that are cleavable under intracellular conditions (e.g., a peptide linker cleavable by an intracellular protease, dipeptide linker, disulfide linker, and hydrolysable linker which are e.g., hydrolysable at a pH of less than 5.5). However, the antibody of the invention may also be used for treating cancer due to its blocking and binding properties on B7-H6 as a modulator of signaling cascades involved in cancer.

The term "diagnosis" as used herein means the assessment whether a subject suffers from a disease referred to herein, or not. As will be understood by those skilled in the art, such an assessment is usually not intended to be correct for all (i.e. 100%) of the subjects to be identified. The term, however, requires that a statistically significant portion of subjects can be identified (e.g., a cohort in a cohort study). Whether a portion is statistically significant can be determined without further ado by the person skilled in the art using various well known statistic evaluation tools referred to elsewhere herein. Diagnosis according to the present invention includes applications of the method in monitoring, confirmation, and sub-classification of the relevant disease. Moreover, the establishment of a diagnosis as used herein also includes establishing a prognosis for a subject. Such a prognosis is a predictive indicator for the further development of the disease in a future time window, i.e. the predictive window. Thus, a diagnosis as used herein, preferably, encompasses a prediction of whether a subject will improve with respect to the disease or diseases symptoms in the future or whether the disease or symptoms will become worse. Accordingly, the antibody of the invention can be also applied for risk stratification approaches and, thus, for determining the amount of intensive care and hospitalization which will be required for an individual subject suffering from a disease referred to herein.

Preferably, the antibody of the invention for use in diagnosis is either coupled to a detection agent or is capable of recruiting such an agent. A detection agent as used herein encompasses a radioactive isotope (e.g., radioactive isotopes of Iodide Technetium), fluorescent or chemoluminescent agents (e.g., FITC, rhodamin), an enzyme which is capable of generating a detectable signal by converting a substrate (e.g., horseradish peroxidase, firefly luciferase, or beta galactosidase), a fluorescent protein (e.g., green-, blue- or red-fluorescent protein). Suitable detection agents are well known in the art. Also preferably, the antibody to be applied in the method of the present invention can be coupled to an agent that is capable of attracting a detection agent. Such an agent may be biotin. In such a case an avidin- or streptavidin coupled detection agent can be used which upon binding of the biotin of the bound antibody will serve as a detectable marker. Suitable detectable markers in such a case are those referred to above, more preferably, an enzyme shall be used as a detectable marker in such a case. Furthermore, a secondary antibody may be used for detection of the first antibody, i.e. the antibody to be applied in the method of the present invention which is bound to the B7-H6 polypeptide of the sample. Such a secondary antibody shall be coupled to a detectable marker as describe above. Thus, in the latter case, the secondary antibody will upon binding to the first antibody generate a detectable signal and thereby enables the detection of the bound first antibody. The principle of detection of bound antibodies with a secondary antibody is well known in the art and routinely applied, e.g., for determining antibody binding on tissue sections. Dependent on the type of detectable marker, different detection methods can be applied using a reader system for the signal generated by the detectable marker. Such systems include automatic signal reader device, such as an ELISA or RIA reader, but also microscopic device for manual or automatic detection of the detectable signal. Moreover, the reader system may determine additional information of the sample, e.g., a microscopic system may display the cells of a tissue section optically or an automated signal reader may determine further biomarkers comprised by the sample in addition.

The term "cancer" as used herein refers to any malignant neoplasm. The malignant neoplasm refers to diseases resulting from the undesired growth, the invasion, and under certain conditions metastasis of impaired cells in an organism. The cells giving rise to cancer are genetically impaired and have usually lost their ability to control cell division, cell migration behavior, differentiation status and/or cell death machinery. Most cancers form a tumor but some hematopoietic cancers, such as leukemia, do not. The cancer in accordance with the present invention shall comprise cancer cells expressing a B7-H6 polypeptide as specified elsewhere herein. Preferred types of cancer are selected from the group consisting of: T cell lymphoma, myeloid leukemia, colon carcinoma, B cell lymphoma, melanoma, or cervical carcinoma. Symptoms and staging systems for the different cancers are well known in the art and described in standard text books of pathology. Cancer as used herein encompasses any stage, grade, morphological feature, invasiveness, aggressiveness or malignancy of the cancer or the tissue or organ affected thereby.

The present invention further relates to an antibody of the invention for use in the treatment or diagnosis of an inflammatory disease.

Preferably, the antibody of the invention for use in treating an inflammatory disease is either coupled to an anti-inflammation agent or is capable of recruiting such an agent as specified elsewhere herein. However, the antibody of the invention may also be used for an inflammatory disease due to its blocking and binding properties on B7-H6 as a modulator of signaling cascades involved in inflammation.

Preferably, the antibody of the invention for use in diagnosis is either coupled to a detection agent or is capable of recruiting such an agent as specified elsewhere herein.

The term "inflammatory disease" as used herein refers to a tissue response involving inflammatory cytokines and inflammatory cell infiltrates in response to an injury or destruction of tissue. The inflammatory disease in accordance with the present invention shall comprise a viral infection, and bacterial infection. In addition, autoimmune diseases such as diabetes, multiple sclerosis and inflammatory bowl disease are included.

If follows from the above that the present invention also relates to a method for diagnosing cancer in a sample of a subject suspected to suffer from cancer comprising:
a) contacting the sample with the antibody of the invention under conditions which allow for binding of said antibody to its epitope on the B7-H6 polypeptide; and
b) determining binding of the antibody to the said epitope, whereby cancer is diagnosed.

The term "diagnosing" as used herein means the assessment whether a subject suffers from a disease referred to herein, or not. As will be understood by those skilled in the art, such an assessment is usually not intended to be correct for all (i.e. 100%) of the subjects to be identified. The term, however, requires that a statistically significant portion of subjects can be identified (e.g., a cohort in a cohort study). Whether a portion is statistically significant can be determined without further ado by the person skilled in the art using various well known statistic evaluation tools referred to elsewhere herein. Diagnosis according to the present invention includes applications of the method in monitoring, confirmation, and sub-classification of the relevant disease. Moreover, the establishment of a diagnosis as used herein also includes establishing a prognosis for a subject. Such a prognosis is a predictive indicator for the further development of the disease in a future time window, i.e. the predictive window. Thus, a diagnosis as used herein, preferably, encompasses a prediction of whether a subject will improve with respect to the disease or diseases symptoms in the future or whether the disease or symptoms will become worse. Accordingly, the antibody of the invention can be also applied for risk stratification approaches and, thus, for determining the amount of intensive care and hospitalization which will be required for an individual subject suffering from a disease referred to herein.

The aforementioned method for diagnosing cancer in a sample of the subject also, preferably, encompasses the step of recommending an anti-cancer therapy for a subject based on the diagnostic result obtained by the method. The term "recommending" as used herein refers to making a recommendation for an anti-cancer therapy or excluding (i.e. not recommending) a certain anti cancer therapy for a subject. Such a recommendation shall serve optionally together with other information, e.g., information from histopathological investigations, as a basis for a clinician to apply a certain anti-cancer therapy for an individual subject, or not. Based on the diagnosis of the present invention, i.e. the diagnosis of cancer or no cancer, a recommendation for an anti-cancer therapy will be made. It will be understood that only in cases where the diagnosis of cancer has been established by the method of the present invention, the recommendation for the anti-cancer therapy shall be made. In cases where no cancer is established as diagnosis based on the method of the present invention, the recommendation would be to refrain from an anti-cancer therapy. As set forth above, further information from the subject from which the sample originates can be used as well for improving the recommendation. In an aspect, a combined anti-cancer therapy, e.g., with different anti tumor drugs, can be recommended if the method of the present invention identifies cancer cells but if further cancer cells which are not identified by the method of the present invention are detected in the investigated cancer, e.g., by histopathological analyses.

The term "sample" refers to a sample of separated cells or to a sample from a tissue or an organ. Tissue or organ samples may be obtained from any tissue or organ by, e.g., biopsy. Separated cells may be obtained from the body fluids, such as lymph, blood, plasma, serum, liquor and other, or from the tissues or organs by separating techniques such as centrifugation or cell sorting. Preferably, the sample is a tissue or body fluid sample which expresses or produces the polypeptides referred to herein. The sample can be obtained from the subject by routine techniques which are well known to the person skilled in the art, e.g., open biopsy including aspiration of tissue or cellular material from a subject. For those areas which cannot be easily reached via an open biopsy, a surgery and, preferably, minimal invasive surgery can be performed.

The term "subject" as used herein relates to animals, preferably mammals, and, more preferably, humans. The method of the present invention shall be applied for subjects suspected to suffer from cancer. A subject suspect to suffer from cancer is either a subject exhibiting clinically apparent symptoms of the cancer or is a subject having an increased predisposition for cancer. In the context of large scale diagnostic screening trials, a subject suspected to suffer from cancer can be even a healthy subject, i.e., a subject who does not show symptoms of the disease nor a subject having a predisposition therefor.

The terms "contacting" and "contacting the sample" as used herein refer to bringing the antibody and the sample into physical contact thereby allowing specific binding of the antibody to the epitope on the B7-H6 polypeptide if comprised by the sample. It will be understood that contacting as meant herein is carried out for a time and under conditions sufficient for allowing the antibody to bind specifically to the B7-H6 polypeptide. Depending on the nature of the sample, pre-treatment steps might be necessary in order to release the B7-H6 polypeptide or to de-mask the epitope in the B7-H6 polypeptide so that the antibody has access and can specifically bind thereto. Moreover, dependent on the kind of sample, the handling might be different. For example, a tissue sample which shall be analyzed for the presence or absence of a B7-H6 polypeptide is, preferably, homogenized and the proteins comprised by the tissue are isolated and separated, e.g., by SDS PAGE or other protein separation methods known by a skilled artisan. The separated proteins are analyzed for the presence or absence of the B7-H6 polypeptide by immunological methods such as Western Blot using the antibody defined herein above. These methods also include incubation steps which allow specific binding of the antibody to the B7-H6 polypeptide. In order to increase the specificity washing steps are to be carried out. How to carry out such measures is well known to the person skilled in the art. If a tissue section is used as a sample (i.e. a tissue section sample), it will be understood that it is envisaged to analyze not only the presence or absence of the B7-H6 polypeptide but also the cellular or sub cellular localization thereof. Accordingly, the tissue shall be kept intact and may be also stained by histochemical staining techniques prior or after antibody binding. Suitable techniques which allow for immunostaining of tissue sections are well known to the person skilled in the art. Dependent on whether the tissue section sample has been embedded in an embedding medium, such as paraffin, removal of said embedding medium might be necessary. The relevant techniques are also well known in the art.

The term "determining" as used herein refers to the detection of the antibody which is specifically bound to the B7-H6 polypeptide comprised by the sample, if any. Detection methods for antibodies which are specifically bound to an antigen are also well known in the art. Preferably, the antibody to be applied in the method of the present invention itself can be coupled to a detectable marker such as a radioactive isotope (e.g., radioactive isotopes of Iodide Technetium), fluorescent or chemoluminescent agents (e.g., FITC, rhodamin), an enzyme which is capable of generating a detectable signal by converting a substrate (e.g., horseradish peroxidase, firefly luciferase, or beta galactosidase), a fluorescent protein (e.g., green-, blue- or red-fluorescent protein). Suitable detectable markers are well known in the art. Also preferably, the antibody to be applied in the method of the present invention can be coupled to an agent that is capable of attracting a detection agent. Such an agent may be biotin. In such a case an avidin- or streptavidin coupled detection agent can be used which upon binding of the biotin of the bound antibody will serve as a detectable marker. Suitable detectable markers in such a case are those referred to above, more preferably, an enzyme shall be used as a detectable marker in such a case. Furthermore, a secondary antibody may be used for detection of the first antibody, i.e. the antibody to be applied in the method of the present invention which is bound to the B7-H6 polypeptide of the sample. Such a secondary antibody shall be coupled to a detectable marker as describe above. Thus, in the latter case, the secondary antibody will upon binding to the first antibody generate a detectable signal and thereby enables the detection of the bound first antibody. The principle of detection of bound antibodies with a secondary antibody is well known in the art and routinely applied, e.g., for determining antibody binding on tissue sections. Dependent on the type of detectable marker, different detection methods can be applied using a reader system for the signal generated by the detectable marker. Such systems include automatic signal reader device, such as an ELISA or RIA reader, but also microscopic device for manual or automatic detection of the detectable signal. Moreover, the reader system may determine additional information of the sample, e.g., a microscopic system may display the cells of a tissue section optically or an automated signal reader may determine further biomarkers comprised by the sample in addition.

In a preferred embodiment of the method of the present invention, the cancer is T cell lymphoma, myeloid leukemia, colon carcinoma, B cell lymphoma, melanoma, or cervical carcinoma.

The present invention also provides a method for diagnosing an inflammatory disease in a sample of a subject suspected to suffer from an inflammatory disease comprising:
a) contacting the sample with the antibody of invention under conditions which allow for binding of said antibody to its epitope on the B7-H6 polypeptide; and
b) determining binding of the antibody to the said epitope, whereby the inflammatory disease is diagnosed.

Explanations of the terms made in connection with the method for diagnosing cancer or other embodiments elsewhere herein apply mutatis mutandis for the terms in connection with the aforementioned method except as specified otherwise herein below.

The term "subject" as used herein relates to animals, preferably mammals, and, more preferably, humans. The method of the present invention shall be applied for subjects suspected to suffer from an inflammatory disease. A subject suspect to suffer from an inflammatory disease is either a subject exhibiting clinically apparent symptoms of the an inflammatory disease or is a subject having an increased predisposition for an inflammatory disease. In the context of large scale diagnostic screening trials, a subject suspected to suffer from an inflammatory disease can be even a healthy subject, i.e. a subject who does not show symptoms of the disease nor a subject having a predisposition therefor.

As discussed elsewhere herein, the inflammatory disease referred to above is, preferably, a viral infection.

The invention also relates to a device for diagnosing cancer or an inflammatory disease in a sample comprising:
a) an analyzing unit comprising the antibody of the invention; and
b) a detector which detects binding of the antibody in the analyzing unit to its epitope on the B7-H6 polypeptide.

The term "device" as used herein relates to a system comprising at least the aforementioned analyzing unit and the evaluation unit operatively linked to each other. How to link the units of the device in an operating manner will depend on the type of units included into the device. For example, where units for automatic analysis of a sample are applied, the data obtained by said automatically operating analyzing unit can be processed by, e.g., a computer program in order to obtain the desired results by the evaluation unit. Preferably, the units are comprised by a single device in such a case. The analyzing unit may comprise the antibody in immobilized form on a solid support. Such an analyzing unit is particular useful for liquid samples. The sample to be investigated with the device of the present invention is preferably a tissue sample and, more preferably, a tissue section sample. Thus, in another aspect, the antibody may be comprised in a detection solution which will be applied to tissue samples such as tissue section by the analyzing unit. The detection solution can be stored in the analyzing unit or a separate vial, even outside the device. The evaluation unit, preferably a computer or data processing device, comprises implemented rules, i.e. an algorithm, for evaluating the binding determined by the analyzing unit whereby the binding is evaluated into significant or non-significant binding based on the signal type, strength and, in the case of tissue samples, position of the signal with respect to the tissue. For samples which are evaluated to show non-significant binding the diagnosis "no cancer" will be established. If significant binding is obtained as result of the evaluation, the diagnosis cancer shall be established.

Preferably, the device in its evaluation unit also comprises an implemented expert system with an algorithm that is adapted for making recommendations based on the established diagnosis for a suitable therapy or treatment as set forth elsewhere herein in more detail.

In a preferred embodiment of the device of the present invention, said sample is a tissue or body fluid sample.

Finally, the present invention relates to a kit for diagnosing cancer or an inflammatory disease comprising the antibody of the invention and, preferably, an agent for detection of binding of said antibody to its epitope on the B7-H6 polypeptide.

The term "kit" as used herein refers to a collection of the aforementioned antibody and instructions provided in a ready-to-use manner for diagnosing cancer in a sample. The antibody and the instructions are, preferably, provided in a single container. Preferably, the kit also comprises further components which are necessary for carrying out the diagnosis. Such components may be auxiliary agents which are required for the detection of the antibody binding, agents for pre-treating the sample to be analyzed or calibration standards.

All references cited in this specification are herewith incorporated by reference with respect to their entire disclosure content and the disclosure content specifically mentioned in this specification.

EXAMPLES

The following Examples shall merely illustrate the invention. They shall not be construed, whatsoever, to limit the scope of the invention.

Example 1: Method for Immunization to Obtain Anti-B7-H6 Monoclonal Antibody (mAb) 1.18

Six weeks old BALB/c mice were immunized with 100 µg of a B7-H6-Ig-fusionprotein consisting of the extracellular domain of B7-H6 fused to an IgG1-Fc domain (B7-H6-Ig-FP) shown in FIG. 1 in complete Freud's Adjuvant injected s.c. at four different sites. Three weeks later, 100 µg B7-H6-Ig-FP was injected i.p. in PBS. After three weeks, BA/F3 (pro-B cells)-B7-H6 transfectants ($2\times10^7$ cells) in PBS were injected i.p. Two months later, 100 µg B7-H6-Ig-FP in PBS was applied i.p. After three weeks, injection with BA/F3-B7-H6 transfectants ($2\times10^7$ cells) in PBS i.p. was performed and five days later spleen cells were fused with Ag8 mouse myeloma cells. 910 hybridoma were screened by flow cytometry for binding of produced immunoglobulins to BA/F3-B7-H6 cells. Additionally, 480 clones were screened by ELISA for binding to the B7-H6-Ig-FP. Anti-B7-H6 clone 1.18 was selected for further studies, because it stained BA/F3-B7-H6 transfectants and not control vector transduced BA/F3 cells at high levels and it bound to cell lines expressing B7-H6 endogenously at high levels.

Example 2: Binding of Anti-B7-H6 mAb 1.18 to B7-H6-Ig-FP by ELISA and to BA/F3-B7-H6 Transfected Cells by Flow Cytometry For ELISA: B7-H6-Ig-FP (3 µg/ml) was immobilized on ELISA plates and incubated with the indicated concentrations of anti-B7-H6 mAb 1.18 and developed with HRP-conjugated mAbs.

For flow cytometry: BA/F3 or BA/F3-B7-H6 transfectants were stained with anti-B7-H6 mAb 1.18 (2 µg/ml), the isotype controls, NKp30-FP and a control FP and PE-conjugated secondary mAbs.

The data depict binding of anti-B7-H6 mAb 1.18 to B7-H6-Ig-FP by ELISA and to BA/F3-B7-H6 transfected cells by flow cytometry.

Example 3: Binding of Anti-B7-H6 1.18 mAb Involves the IgV Domain of B7-H6

The following constructs based on the pcDNA3.1 with CD8-leader peptide and a C-terminal HA-tag encoding for the following portions of B7-H6 were prepared:
B7-H6_1 (amino acids 24-454)
B7-H6_2 (amino acids 83-454)
B7-H6_3 (amino acids 141-454)
B7-H6_4 (amino acids 190-454)
B7-H6_5 (amino acids 239-454)

Figure 3:
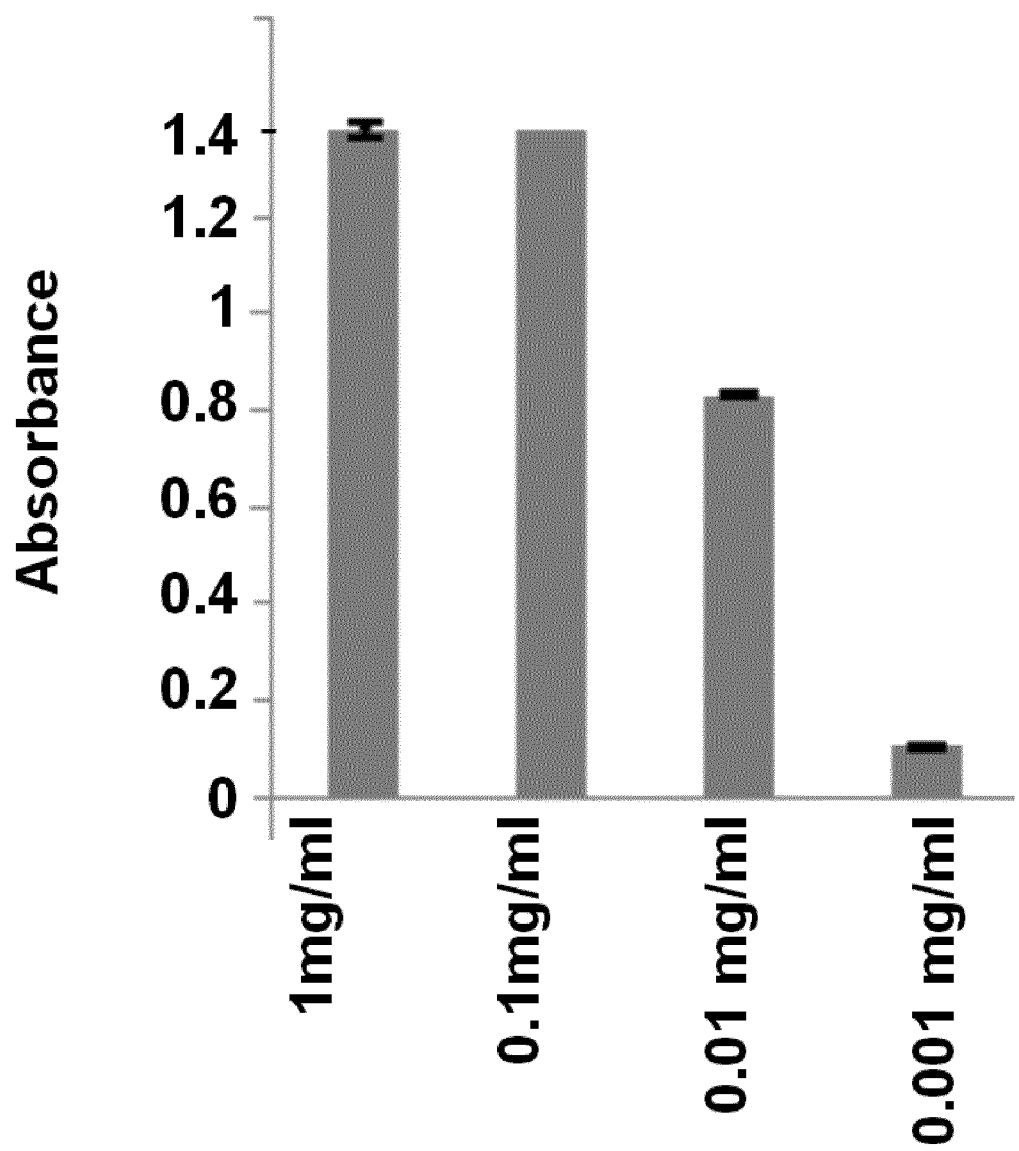
FIG. 3 shows that the anti-B7-H6 clone 1.18 reacts with B7-H6 using an enzyme-linked immunoabsorbant assay (ELISA).
Figure 4A:
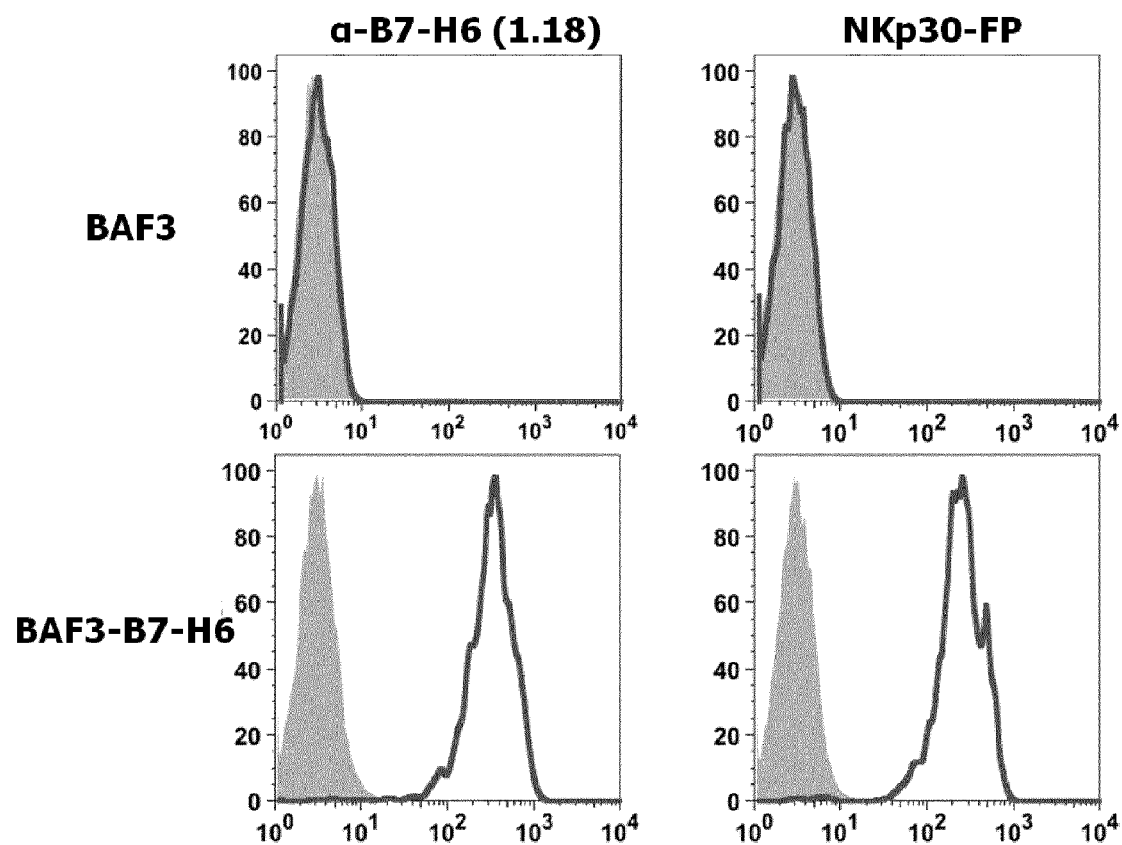
FIG. 4a depicts that the anti-B7-H6 clone 1.18 binds to B7-H6 on transfectants (BA/F3-B7-H6) using fluorescence-activated cell sorting (FACS).
Figure 4B:
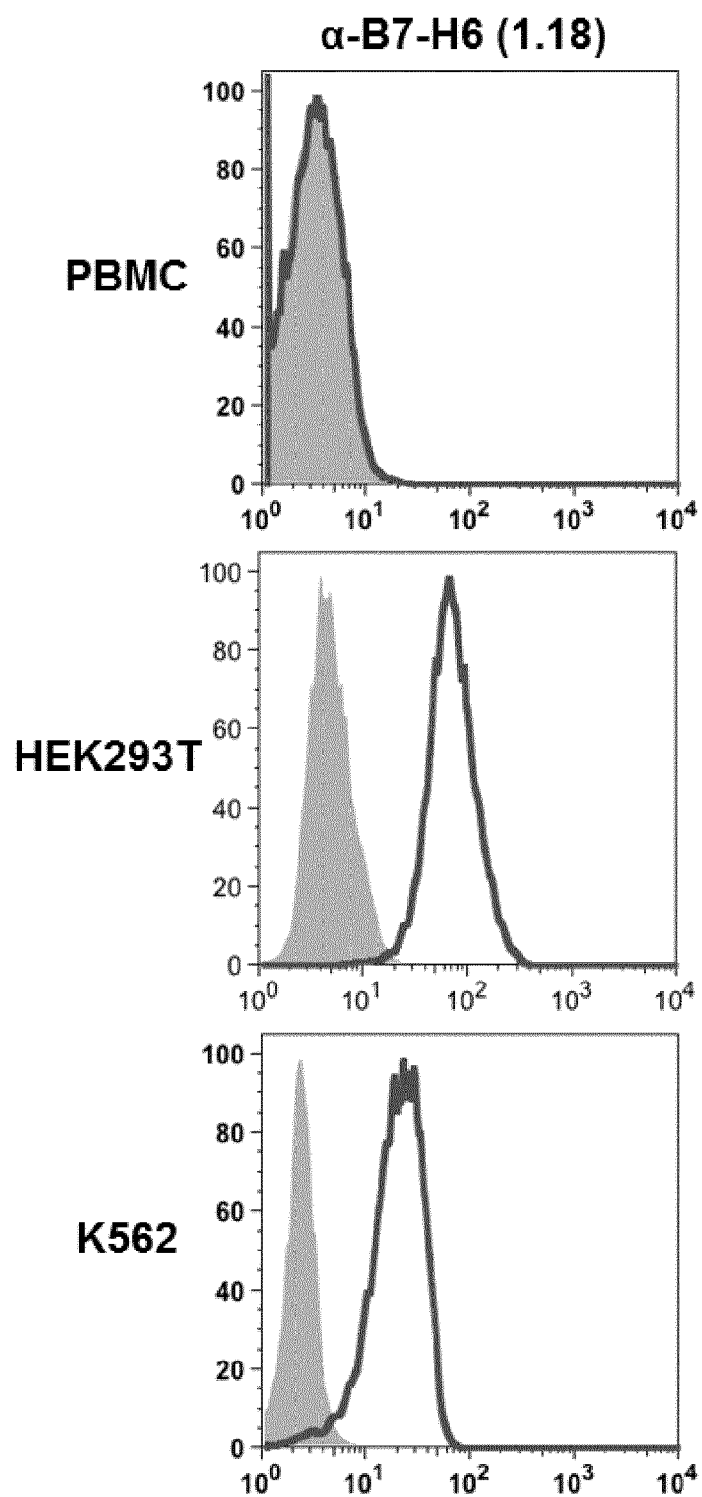
FIG. 4b shows that the anti-B7-H6 clone 1.18 binds to B7-H6 on cell lines (haematopoietic and solid tumor origin), but not to healthy peripheral blood mononuclear cells (PBMCs).
Figure 5:
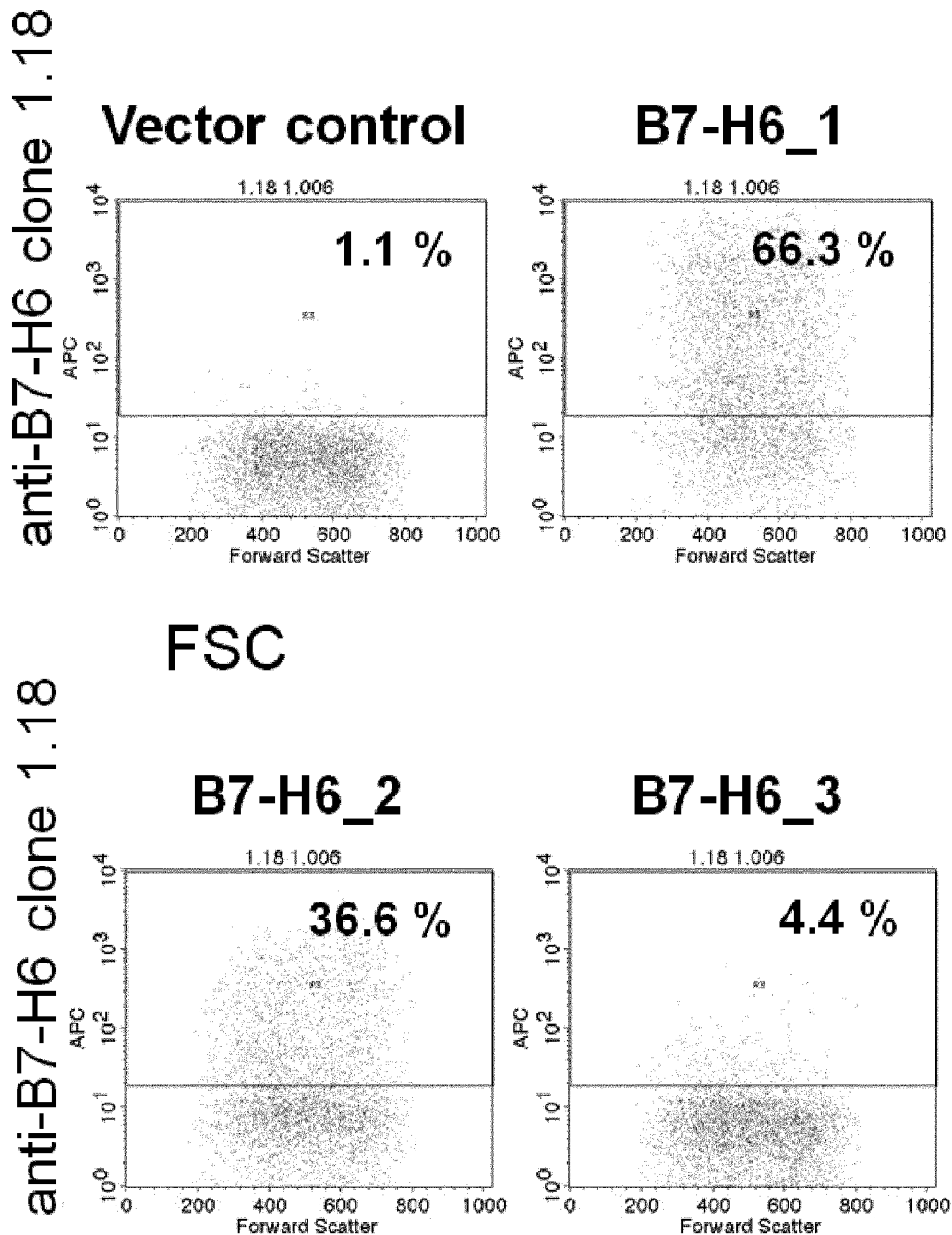
FIG. 5 shows that a portion of the IgV domain of B7-H6 is involved in binding of anti-B7-H6 clone 1.18.
Figure 5:
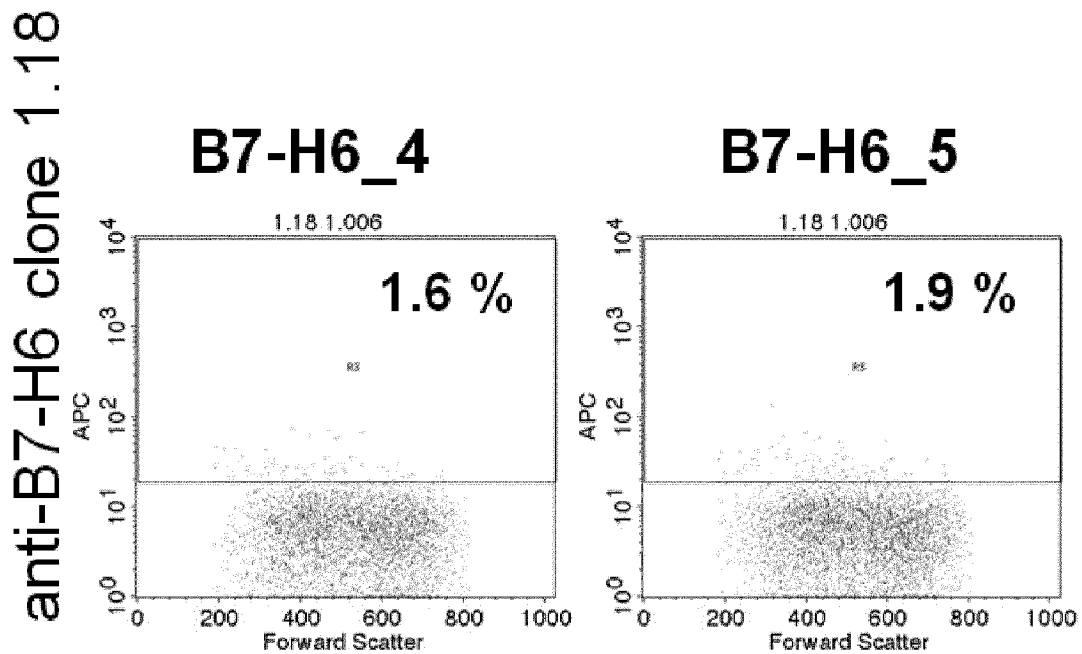

Resulting plasmids were transiently transfected in HEK cells and subsequently stained with the anti-B7-H6 1.18 mAb as described in Example 2. As can be seen in FIG. 5, the anti-B7-H6 1.18 mAb bound to B7-H6_1 (amino acids 24-454) and B7-H6_2 (amino acids 83-454), but not to B7-H6_3 (amino acids 141-454) indicating that amino acids 83-141 of B7-H6 (GDHQEAFRPGAIVSPWRLKSG-DASLRLPGIQLEEAGEYRCEVVVTPLKAQGT VQLEVV, as shown in SEQ ID NO: 22 and FIGS. 1 and 2) are involved in the binding of anti-B7-H6 mAb 1.18. All proteins of truncated B7-H6 were expressed and were detectable by western blotting using the anti-HA-tag mAb.

Example 4: Binding of Anti-B7-H6 mAb 1.18 to Cell Lines of Different Origin

Cell lines of different origin were stained with anti-B7-H6 mAb 1.18 and analyzed by flow cytometry as described in Example 2. The data reveal binding of anti-B7-H6 mAb 1.18 to cell lines of different origin.

Example 5: Quantitative Real-Time PCR to Determine B7-H6 mRNA Expression

RNA was isolated from tumor cell lines using the RNeasy Mini kit (Qiagen), contaminating DNA was removed using TURBO DNase (Ambion) and the RNA was reverse transcribed using the ProtoScript M-MuLV First Strand cDNA synthesis kit (NEB). Quantitative real-time PCR was performed using the SYBR Green I Master and LightCycler480 (Roche). Specific primers for B7-H6 (GACCTGGAGC-CATTGTGTCT as shown in SEQ ID NO: 23 and AAGCTG-GACTGTTCCCTGTG as shown in SEQ ID NO: 24) and the housekeeping gene GAPDH (GCAAATTCCATG-GCACCGT as shown in SEQ ID NO: 25 and TCGC-CCCACTTGATTTTGG as shown in SEQ ID NO: 26) were used in order to calculate the B7-H6 mRNA expression level relative to GAPDH. The data depict that cell lines of different origin that are stained with anti-B7-H6 mAb 1.18 express mRNA of B7-H6 in different amounts.

Example 6: Immunohistochemical Staining of B7-H6 on Cytospins of Ba/F3-B7-H6 Transfectants Acetone-fixed cytospins of a 1:1 mixture of Ba/F3 and Ba/F3-B7-H6 cells were stained using the Dual Envision+ System-HRP (Dako). After blocking endogenous peroxidase activity, cytospins were blocked with 10% goat serum and 0.1 mg/ml human IgG. The cytospins were incubated with 5 µg/ml anti-B7-H6 mAb 1.18 or a mouse IgG1 isotype control (clone 11711, R&D) in Dako antibody diluent, washed and incubated with Dako Peroxidase labeled polymer conjugated to goat anti-mouse and goat anti-rabbit immunoglobulins. After incubation with 3,3'-diaminobenzidine (DAB) substrate solution, cell nuclei were counterstained with Hematoxylin and mounted cyotospins were analyzed by light microscopy. The data reveal that anti-B7-H6 mAb 1.18 stains B7-H6 Ba/F3-B7-H6 transfectants on cytospins.

Example 7: Degranulation of Primary NK Cells After Co-Culture with BA/F3 Cells Transduced with B7-H6

Primary NK cells expanded with IL-2 for 14 days were cultured in media, with BA/F3, BA/F3-B7-H6 (ligand for NKp30) or BA/F3-MICA (ligand for the activating receptor NKG2D) cells in the presence of a PE-conjugated anti-CD107 mAb for 5 h. Degranulation of NK cells was determined as percentages of CD107-positive NK cells after co-culture by flow cytometry. Error bars depict mean+/−SD of triplicate cultures. The data reveal that BA/F3-B7-H6 cells induce degranulation of primary NK cells.

The invention claimed is:

1. An antibody which specifically binds to an epitope formed by a portion of the extracellular domain of the B7-H6 polypeptide, said portion consisting of an amino acid sequence as shown in SEQ ID NO: 22.

2. The antibody of claim 1, wherein the antibody comprises complementarity determining regions (CDRs) encoded by SEQ ID NOs: 5, 7, 9, 15, 17, and 19.

3. The antibody of claim 1, wherein the antibody is a monoclonal antibody.

4. The antibody of claim 1, wherein the antibody is the antibody produced by the hybridoma cell clone deposited under accession number DSM ACC 3117 at the DSMZ, Braunschweig, Germany under the conditions of the Budapest Treaty on Feb. 2, 2011.

5. A method for diagnosing cancer in a sample of a subject suspected to suffer from cancer comprising:
(a) contacting the sample with the antibody of claim 1 under conditions which allow for binding of the antibody to its epitope on the B7-H6 polypeptide; and
(b) determining binding of the antibody to the the epitope, whereby cancer s diagnosed if binding is detected.

6. The method of claim 5, wherein the cancer is T cell lymphoma, myeloid leukemia, colon carcinoma, B cell lymphoma, melanoma, or cervical carcinoma.

7. The method of claim 5, wherein the sample is a tissue or body fluid sample.

8. A kit for diagnosing cancer comprising the antibody of claim 1, and an agent for detection of binding of the antibody to its epitope on the B7-H6 polypeptide.

* * * * *

SEQUENCE LISTING

<160> NUMBER OF SEQ ID NOS: 26

<210> SEQ ID NO 1
<211> LENGTH: 1653
<212> TYPE: DNA
<213> ORGANISM: Homo sapiens

<400> SEQUENCE: 1

| | | | | | |
|---|---|---|---|---|---|
| atggaacaac | ggggacagaa | cgccccggcc | gcttcggggg | cccggaaaag | gcacggccca | 60 |
| ggacccaggg | aggcgcgggg | agccaggcct | gggccccggg | tccccaagac | ccttgtgctc | 120 |
| gttgtcgccg | cggtcctgct | gttggtctca | gctgagtctg | ctctggaatc | cgatctgaaa | 180 |
| gtagagatga | tggcagggggg | gactcagatc | acacccctga | tgacaatgt | caccatattc | 240 |
| tgcaatatct | tttattccca | accctcaac | atcacgtcta | tgggtatcac | ctggttttgg | 300 |
| aagagtctga | cgtttgacaa | agaagtcaaa | gtctttgaat | tttttggaga | tcaccaagag | 360 |
| gcattccgac | ctgagccat | tgtgtctcca | tggaggctga | agagtgggga | cgcctcactg | 420 |
| cggctgcctg | gaatccagct | ggaggaagca | ggagagtacc | gatgtgaggt | ggtggtcacc | 480 |
| cctctgaagg | cacagggaac | agtccagctt | gaagttgtgg | cttccccagc | cagcagattg | 540 |
| ttgctggatc | aagtgggcat | gaaagagaat | gaagacaaat | atatgtgtga | gtcaagtggg | 600 |
| ttctacccag | aggctattaa | tataacatgg | gagaagcaga | cccagaagtt | tccccatccc | 660 |
| atagagattt | ctgaggatgt | catcactggt | cccaccatca | gaatatgga | tggcacattt | 720 |
| aatgtcacta | gctgcttgaa | gctgaactcc | tctcaggaag | accctgggac | tgtctaccag | 780 |
| tgtgtggtac | ggcatgcgtc | cttgcatacc | cccttgagga | gcaactttac | cctgactgct | 840 |
| gctcggcaca | gtctttctga | aactgagaag | acagataatt | tttccattca | ttggtggcct | 900 |
| gatatcactc | acacatgccc | accgtgccca | gcacctgaag | ccgagggcgc | gccgtcagtc | 960 |
| ttcctcttcc | ccccaaaacc | caaggacacc | ctcatgatct | cccggacccc | tgaggtcaca | 1020 |
| tgcgtggtgg | tggacgtgag | ccacgaagac | cctgaggtca | agttcaactg | gtacgtggac | 1080 |
| ggcgtggagg | tgcataatgc | caagacaaag | ccgcgggagg | agcagtacaa | cagcacgtac | 1140 |
| cgtgtggtca | gcgtcctcac | cgtcctgcac | caggactggc | tgaatggcaa | ggagtacaag | 1200 |
| tgcaaggtct | ccaacaaagc | cctcccagcc | cccatcgaga | aaaccatctc | caaagccaaa | 1260 |
| gggcagcccc | gagaaccaca | ggtgtacacc | ctgcccccat | cccgggagga | gatgaccaag | 1320 |
| aaccaggtca | gcctgcagcc | ggagaacaac | tacaagacca | cgcctcccgt | gctggactcc | 1380 |
| gacggctcct | tcttcctcta | tagcaagctc | accgtggaca | agagcaggtg | gcagcagggg | 1440 |
| aacgtcttct | catgctccgt | gatgcatgag | gctctgcaca | accactacac | gcagaagagc | 1500 |
| ctctccctgt | ctccgggtaa | acatatggga | ggtgacgaaa | agaccaccgg | ctggcgcggc | 1560 |
| ggccacgtgg | tggaaggcct | ggccggcgaa | ctggaacagc | tgcgcgcccg | cctggaacac | 1620 |
| cacccacagg | gccagcgcga | accatgactc | gag | | | 1653 |

<210> SEQ ID NO 2
<211> LENGTH: 548
<212> TYPE: PRT
<213> ORGANISM: Homo sapiens

<400> SEQUENCE: 2

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
            20                  25                  30

```
Arg Val Pro Lys Thr Leu Val Leu Val Ala Ala Val Leu Leu Leu
         35                  40                  45

Val Ser Ala Glu Ser Ala Leu Glu Ser Asp Leu Lys Val Glu Met Met
 50                  55                  60

Ala Gly Gly Thr Gln Ile Thr Pro Leu Asn Asp Asn Val Thr Ile Phe
 65                  70                  75                  80

Cys Asn Ile Phe Tyr Ser Gln Pro Leu Asn Ile Thr Ser Met Gly Ile
                 85                  90                  95

Thr Trp Phe Trp Lys Ser Leu Thr Phe Asp Lys Glu Val Lys Val Phe
                100                 105                 110

Glu Phe Phe Gly Asp His Gln Glu Ala Phe Arg Pro Gly Ala Ile Val
                115                 120                 125

Ser Pro Trp Arg Leu Lys Ser Gly Asp Ala Ser Leu Arg Leu Pro Gly
        130                 135                 140

Ile Gln Leu Glu Glu Ala Gly Glu Tyr Arg Cys Glu Val Val Val Thr
145                 150                 155                 160

Pro Leu Lys Ala Gln Gly Thr Val Gln Leu Glu Val Val Ala Ser Pro
                165                 170                 175

Ala Ser Arg Leu Leu Leu Asp Gln Val Gly Met Lys Glu Asn Glu Asp
        180                 185                 190

Lys Tyr Met Cys Glu Ser Ser Gly Phe Tyr Pro Glu Ala Ile Asn Ile
            195                 200                 205

Thr Trp Glu Lys Gln Thr Gln Lys Phe Pro His Pro Ile Glu Ile Ser
        210                 215                 220

Glu Asp Val Ile Thr Gly Pro Thr Ile Lys Asn Met Asp Gly Thr Phe
225                 230                 235                 240

Asn Val Thr Ser Cys Leu Lys Leu Asn Ser Ser Gln Glu Asp Pro Gly
                245                 250                 255

Thr Val Tyr Gln Cys Val Val Arg His Ala Ser Leu His Thr Pro Leu
                260                 265                 270

Arg Ser Asn Phe Thr Leu Thr Ala Ala Arg His Ser Leu Ser Glu Thr
        275                 280                 285

Glu Lys Thr Asp Asn Phe Ser Ile His Trp Trp Pro Asp Ile Thr His
        290                 295                 300

Thr Cys Pro Pro Cys Pro Ala Pro Glu Ala Glu Gly Ala Pro Ser Val
305                 310                 315                 320

Phe Leu Phe Pro Pro Lys Pro Lys Asp Thr Leu Met Ile Ser Arg Thr
                325                 330                 335

Pro Glu Val Thr Cys Val Val Val Asp Val Ser His Glu Asp Pro Glu
                340                 345                 350

Val Lys Phe Asn Trp Tyr Val Asp Gly Val Glu Val His Asn Ala Lys
        355                 360                 365

Thr Lys Pro Arg Glu Glu Gln Tyr Asn Ser Thr Tyr Arg Val Val Ser
    370                 375                 380

Val Leu Thr Val Leu His Gln Asp Trp Leu Asn Gly Lys Glu Tyr Lys
385                 390                 395                 400

Cys Lys Val Ser Asn Lys Ala Leu Pro Ala Pro Ile Glu Lys Thr Ile
                405                 410                 415

Ser Lys Ala Lys Gly Gln Pro Arg Glu Pro Gln Val Tyr Thr Leu Pro
            420                 425                 430

Pro Ser Arg Glu Glu Met Thr Lys Asn Gln Val Ser Leu Gln Pro Glu
        435                 440                 445
```

```
Asn Asn Tyr Lys Thr Thr Pro Pro Val Leu Asp Ser Asp Gly Ser Phe
    450                 455                 460
Phe Leu Tyr Ser Lys Leu Thr Val Asp Lys Ser Arg Trp Gln Gln Gly
465                 470                 475                 480
Asn Val Phe Ser Cys Ser Val Met His Glu Ala Leu His Asn His Tyr
                485                 490                 495
Thr Gln Lys Ser Leu Ser Leu Ser Pro Gly Lys His Met Gly Gly Asp
            500                 505                 510
Glu Lys Thr Thr Gly Trp Arg Gly Gly His Val Val Glu Gly Leu Ala
        515                 520                 525
Gly Glu Leu Glu Gln Leu Arg Ala Arg Leu Glu His His Pro Gln Gly
    530                 535                 540
Gln Arg Glu Pro
545
```

<210> SEQ ID NO 3
<211> LENGTH: 117
<212> TYPE: PRT
<213> ORGANISM: Artificial Sequence
<220> FEATURE:
<223> OTHER INFORMATION: Amino acid sequence of the heavy chain of
      anti-B7-H6 clone 1.18 (IGHV/IGHD/IGHJ)

<400> SEQUENCE: 3

```
Asp Val Lys Leu Val Glu Ser Gly Gly Gly Leu Val Lys Pro Gly Gly
1               5                   10                  15
Ser Leu Lys Leu Ser Cys Ala Ala Ser Gly Phe Thr Phe Ser Ser Tyr
            20                  25                  30
Thr Met Ser Trp Val Arg Gln Thr Pro Glu Lys Arg Leu Glu Trp Val
        35                  40                  45
Ala Thr Ile Asn Asn Gly Gly Ser Tyr Thr Tyr Tyr Pro Asp Ser Val
    50                  55                  60
Lys Gly Arg Phe Thr Ile Ser Arg Asp Asn Ala Lys Asn Thr Leu Tyr
65                  70                  75                  80
Leu Gln Met Ser Ser Leu Lys Ser Glu Asp Thr Ala Ile Tyr Tyr Cys
                85                  90                  95
Tyr Gly Tyr Asp Pro Ala Trp Phe Ala Tyr Trp Gly Gln Gly Thr Leu
            100                 105                 110
Val Thr Val Ser Ala
        115
```

<210> SEQ ID NO 4
<211> LENGTH: 75
<212> TYPE: DNA
<213> ORGANISM: Artificial Sequence
<220> FEATURE:
<223> OTHER INFORMATION: Nucleic acid sequence of the heavy chain of
      anti-B7-H6 clone 1.18 (IGHV/IGHD/IGHJ), FR1

<400> SEQUENCE: 4
gacgtgaagc tggtggagtc tgggggaggc ttagtgaagc ctggagggtc cctgaaactc    60
tcctgtgcag cctct                                                    75

<210> SEQ ID NO 5
<211> LENGTH: 24
<212> TYPE: DNA
<213> ORGANISM: Artificial Sequence
<220> FEATURE:
<223> OTHER INFORMATION: Nucleic acid sequence of the heavy chain of
      anti-B7-H6 clone 1.18 (IGHV/IGHD/IGHJ), CDR1

<210> SEQ ID NO 5
<211> LENGTH: 24
<212> TYPE: DNA
<213> ORGANISM: Artificial Sequence
<220> FEATURE:
<223> OTHER INFORMATION: Nucleic acid sequence of the heavy chain of anti-B7-H6 clone 1.18 (IGHV/IGHD/IGHJ), FR2

<400> SEQUENCE: 5
ggattcactt tcagtagcta tacc                                      24

<210> SEQ ID NO 6
<211> LENGTH: 51
<212> TYPE: DNA
<213> ORGANISM: Artificial Sequence
<220> FEATURE:
<223> OTHER INFORMATION: Nucleic acid sequence of the heavy chain of anti-B7-H6 clone 1.18 (IGHV/IGHD/IGHJ), FR2

<400> SEQUENCE: 6
atgtcttggg ttcgccagac tccggagaag aggctggagt gggtcgcaac c         51

<210> SEQ ID NO 7
<211> LENGTH: 24
<212> TYPE: DNA
<213> ORGANISM: Artificial Sequence
<220> FEATURE:
<223> OTHER INFORMATION: Nucleic acid sequence of the heavy chain of anti-B7-H6 clone 1.18 (IGHV/IGHD/IGHJ), CDR2

<400> SEQUENCE: 7
attaataatg gtggtagtta cacc                                      24

<210> SEQ ID NO 8
<211> LENGTH: 114
<212> TYPE: DNA
<213> ORGANISM: Artificial Sequence
<220> FEATURE:
<223> OTHER INFORMATION: Nucleic acid sequence of the heavy chain of anti-B7-H6 clone 1.18 (IGHV/IGHD/IGHJ), FR3

<400> SEQUENCE: 8
tactatccag acagtgtgaa gggccgattc accatctcca gagacaatgc caagaacacc    60
ctgtacctgc aaatgagcag tctgaagtct gaggacacag ccatttatta ctgc         114

<210> SEQ ID NO 9
<211> LENGTH: 30
<212> TYPE: DNA
<213> ORGANISM: Artificial Sequence
<220> FEATURE:
<223> OTHER INFORMATION: Nucleic acid sequence of the heavy chain of anti-B7-H6 clone 1.18 (IGHV/IGHD/IGHJ), CDR3

<400> SEQUENCE: 9
tatggttacg acccggcctg gtttgcttac                                30

<210> SEQ ID NO 10
<211> LENGTH: 33
<212> TYPE: DNA
<213> ORGANISM: Artificial Sequence
<220> FEATURE:
<223> OTHER INFORMATION: Nucleic acid sequence of the heavy chain of anti-B7-H6 clone 1.18 (IGHV/IGHD/IGHJ), FR4

<400> SEQUENCE: 10
tggggccaag gactctggt cactgtctct gca                             33

<210> SEQ ID NO 11
<211> LENGTH: 428
<212> TYPE: PRT
<213> ORGANISM: Artificial Sequence
<220> FEATURE:
<223> OTHER INFORMATION: Amino acid sequence of the heavy chain of anti-B7-H6 clone 1.18 (IGHV/IGHD/IGHJ/IGHG1), secreted form

<400> SEQUENCE: 11

Asp Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Asn Asn Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Ile Tyr Tyr Cys
                85                  90                  95

Tyr Gly Tyr Asp Pro Ala Trp Phe Ala Tyr Trp Gly Gln Gly Thr Leu
            100                 105                 110

Val Thr Val Ser Ala Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Glu Ser
                165                 170                 175

Asp Leu Tyr Thr Leu Ser Ser Ser Val Thr Val Pro Ser Ser Pro Arg
            180                 185                 190

Pro Ser Glu Thr Val Thr Cys Asn Val Ala His Pro Ala Ser Ser Thr
        195                 200                 205

Lys Val Asp Lys Lys Ile Val Pro Glu Val Ser Ser Val Phe Ile Phe
    210                 215                 220

Pro Pro Lys Pro Lys Asp Val Leu Thr Ile Thr Leu Thr Pro Lys Val
225                 230                 235                 240

Thr Cys Val Val Val Asp Ile Ser Lys Asp Asp Pro Glu Val Gln Phe
                245                 250                 255

Ser Trp Phe Val Asp Asp Val Glu Val His Thr Ala Gln Thr Gln Pro
            260                 265                 270

Arg Glu Glu Gln Phe Asn Ser Thr Phe Arg Ser Val Ser Glu Leu Pro
        275                 280                 285

Ile Met His Gln Asp Trp Leu Asn Gly Lys Glu Phe Lys Cys Arg Val
    290                 295                 300

Asn Ser Ala Ala Phe Pro Ala Pro Ile Glu Lys Thr Ile Ser Lys Thr
305                 310                 315                 320

Lys Gly Arg Pro Lys Ala Pro Gln Val Tyr Thr Ile Pro Pro Pro Lys
                325                 330                 335

Glu Gln Met Ala Lys Asp Lys Val Ser Leu Thr Cys Met Ile Thr Asp
            340                 345                 350

Phe Phe Pro Glu Asp Ile Thr Val Glu Trp Gln Trp Asn Gly Gln Pro
        355                 360                 365

Ala Glu Asn Tyr Lys Asn Thr Gln Pro Ile Met Asn Thr Asn Gly Ser
    370                 375                 380

Tyr Phe Val Tyr Ser Lys Leu Asn Val Gln Lys Ser Asn Trp Glu Ala
385                 390                 395                 400

Gly Asn Thr Phe Thr Cys Ser Val Leu His Glu Gly Leu His Asn His
                    405                 410                 415

His Thr Glu Lys Ser Leu Ser His Ser Pro Gly Lys
        420                 425

<210> SEQ ID NO 12
<211> LENGTH: 498
<212> TYPE: PRT
<213> ORGANISM: Artificial Sequence
<220> FEATURE:
<223> OTHER INFORMATION: Amino acid sequence of the heavy chain of
      anti-B7-H6 clone 1.18 (IGHV/IGHD/IGHJ/IGHG1), membrane bound form

<400> SEQUENCE: 12

Asp Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Asn Asn Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Ile Tyr Tyr Cys
                85                  90                  95

Tyr Gly Tyr Asp Pro Ala Trp Phe Ala Tyr Trp Gly Gln Gly Thr Leu
            100                 105                 110

Val Thr Val Ser Ala Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Glu Ser
                165                 170                 175

Asp Leu Tyr Thr Leu Ser Ser Ser Val Thr Val Pro Ser Ser Pro Arg
            180                 185                 190

Pro Ser Glu Thr Val Thr Cys Asn Val Ala His Pro Ala Ser Ser Thr
        195                 200                 205

Lys Val Asp Lys Lys Ile Val Pro Glu Val Ser Ser Val Phe Ile Phe
    210                 215                 220

Pro Pro Lys Pro Lys Asp Val Leu Thr Ile Thr Leu Thr Pro Lys Val
225                 230                 235                 240

Thr Cys Val Val Val Asp Ile Ser Lys Asp Asp Pro Glu Val Gln Phe
                245                 250                 255

Ser Trp Phe Val Asp Asp Val Glu Val His Thr Ala Gln Thr Gln Pro
            260                 265                 270

Arg Glu Glu Gln Phe Asn Ser Thr Phe Arg Ser Val Ser Glu Leu Pro
        275                 280                 285

Ile Met His Gln Asp Trp Leu Asn Gly Lys Glu Phe Lys Cys Arg Val
    290                 295                 300

Asn Ser Ala Ala Phe Pro Ala Pro Ile Glu Lys Thr Ile Ser Lys Thr
305                 310                 315                 320

Lys Gly Arg Pro Lys Ala Pro Gln Val Tyr Thr Ile Pro Pro Pro Lys
                325                 330                 335

```
Glu Gln Met Ala Lys Asp Lys Val Ser Leu Thr Cys Met Ile Thr Asp
                340                 345                 350

Phe Phe Pro Glu Asp Ile Thr Val Glu Trp Gln Trp Asn Gly Gln Pro
            355                 360                 365

Ala Glu Asn Tyr Lys Asn Thr Gln Pro Ile Met Asn Thr Asn Gly Ser
370                 375                 380

Tyr Phe Val Tyr Ser Lys Leu Asn Val Gln Lys Ser Asn Trp Glu Ala
385                 390                 395                 400

Gly Asn Thr Phe Thr Cys Ser Val Leu His Glu Gly Leu His Asn His
                405                 410                 415

His Thr Glu Lys Ser Leu Ser His Ser Pro Gly Lys Leu Gln Leu Asp
                420                 425                 430

Glu Thr Cys Ala Glu Ala Gln Asp Gly Glu Leu Asp Gly Leu Trp Thr
            435                 440                 445

Thr Ile Thr Ile Phe Ile Ser Leu Phe Leu Leu Ser Val Cys Tyr Ser
450                 455                 460

Ala Ala Val Thr Leu Phe Lys Val Lys Trp Ile Phe Ser Ser Val Val
465                 470                 475                 480

Glu Leu Lys Gln Thr Leu Val Pro Glu Tyr Lys Asn Met Ile Gly Gln
                485                 490                 495

Ala Pro

<210> SEQ ID NO 13
<211> LENGTH: 109
<212> TYPE: PRT
<213> ORGANISM: Artificial Sequence
<220> FEATURE:
<223> OTHER INFORMATION: Amino acid sequence of the light chain of
      anti-B7-H6 clone 1.18 (IGLV/IGLJ)

<400> SEQUENCE: 13

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
            35                  40                  45

Leu Ile Gly Gly Thr Asn Asn Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
            100                 105

<210> SEQ ID NO 14
<211> LENGTH: 75
<212> TYPE: PRT
<213> ORGANISM: Artificial Sequence
<220> FEATURE:
<223> OTHER INFORMATION: Nucleic acid sequence of the light chain of
      anti-B7-H6 clone 1.18 (IGLV/IGLJ), FR1

<400> SEQUENCE: 14

Cys Ala Gly Gly Cys Thr Gly Thr Gly Thr Gly Ala Cys Thr Cys
1               5                   10                  15
```

```
Ala Gly Gly Ala Ala Thr Cys Thr Gly Cys Ala Cys Thr Cys Ala Cys
            20                  25                  30

Cys Ala Cys Ala Thr Cys Ala Cys Cys Thr Gly Thr Gly Ala Ala
            35                  40                  45

Ala Cys Ala Gly Thr Cys Ala Cys Ala Cys Thr Cys Ala Cys Thr Thr
50                  55                  60

Gly Thr Cys Gly Cys Thr Cys Ala Ala Gly Thr
65                  70                  75
```

<210> SEQ ID NO 15
<211> LENGTH: 27
<212> TYPE: DNA
<213> ORGANISM: Artificial Sequence
<220> FEATURE:
<223> OTHER INFORMATION: Nucleic acid sequence of the light chain of anti-B7-H6 clone 1.18 (IGLV/IGLJ), CDR1

<400> SEQUENCE: 15
actggggctg ttacaactag taactat        27

<210> SEQ ID NO 16
<211> LENGTH: 51
<212> TYPE: DNA
<213> ORGANISM: Artificial Sequence
<220> FEATURE:
<223> OTHER INFORMATION: Nucleic acid sequence of the light chain of anti-B7-H6 clone 1.18 (IGLV/IGLJ), FR2

<400> SEQUENCE: 16
gccaactggg tccaagaaaa accagatcat ttattcactg gtctaatagg t        51

<210> SEQ ID NO 17
<211> LENGTH: 9
<212> TYPE: DNA
<213> ORGANISM: Artificial Sequence
<220> FEATURE:
<223> OTHER INFORMATION: Nucleic acid sequence of the light chain of anti-B7-H6 clone 1.18 (IGLV/IGLJ), CDR2

<400> SEQUENCE: 17 ggtaccaac        9

<210> SEQ ID NO 18
<211> LENGTH: 108
<212> TYPE: DNA
<213> ORGANISM: Artificial Sequence
<220> FEATURE:
<223> OTHER INFORMATION: Nucleic acid sequence of the light chain of anti-B7-H6 clone 1.18 (IGLV/IGLJ), FR3

<400> SEQUENCE: 18
aaccgagctc caggtgttcc tgccagattc tcaggctccc tgattggaga caaggctgcc        60
ctcaccatca caggggcaca gactgaggat gaggcaatat atttctgt        108

<210> SEQ ID NO 19
<211> LENGTH: 27
<212> TYPE: DNA
<213> ORGANISM: Artificial Sequence
<220> FEATURE:
<223> OTHER INFORMATION: Nucleic acid sequence of the light chain of anti-B7-H6 clone 1.18 (IGLV/IGLJ), CDR3

<400> SEQUENCE: 19
gctctatggt acagcaacca ctgggtg        27

<210> SEQ ID NO 20
<211> LENGTH: 30
<212> TYPE: DNA
<213> ORGANISM: Artificial Sequence
<220> FEATURE:
<223> OTHER INFORMATION: Nucleic acid sequence of the light chain of
      anti-B7-H6 clone 1.18 (IGLV/IGLJ), FR4

<400> SEQUENCE: 20
ttcggtggag gaaccaaact gactgtcctg                                          30

<210> SEQ ID NO 21
<211> LENGTH: 215
<212> TYPE: PRT
<213> ORGANISM: Artificial Sequence
<220> FEATURE:
<223> OTHER INFORMATION: Amino acid sequence of the light chain of
      anti-B7-H6 clone 1.18 (IGLV/IGLJ/IGLC)

<400> SEQUENCE: 21

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Thr Lys Leu Thr Val Leu Gly Gln Pro
            100                 105                 110

Lys Ser Ser Pro Ser Val Thr Leu Phe Pro Pro Ser Ser Glu Glu Leu
            115                 120                 125

Glu Thr Asn Lys Ala Thr Leu Val Cys Thr Ile Thr Asp Phe Tyr Pro
        130                 135                 140

Gly Val Val Thr Val Asp Trp Lys Val Asp Gly Thr Pro Val Thr Gln
145                 150                 155                 160

Gly Met Glu Thr Thr Gln Pro Ser Lys Gln Ser Asn Asn Lys Tyr Met
                165                 170                 175

Ala Ser Ser Tyr Leu Thr Leu Thr Ala Arg Ala Trp Glu Arg His Ser
            180                 185                 190

Ser Tyr Ser Cys Gln Val Thr His Glu Gly His Thr Val Glu Lys Ser
        195                 200                 205

Leu Ser Arg Ala Asp Cys Ser
    210                 215

<210> SEQ ID NO 22
<211> LENGTH: 58
<212> TYPE: PRT
<213> ORGANISM: Homo sapiens

<400> SEQUENCE: 22

Gly Asp His Gln Glu Ala Phe Arg Pro Gly Ala Ile Val Ser Pro Trp
1               5                   10                  15

Arg Leu Lys Ser Gly Asp Ala Ser Leu Arg Leu Pro Gly Ile Gln Leu
            20                  25                  30

```
Glu Glu Ala Gly Glu Tyr Arg Cys Glu Val Val Val Thr Pro Leu Lys
        35                  40                  45
Ala Gln Gly Thr Val Gln Leu Glu Val Val
    50                  55

<210> SEQ ID NO 23
<211> LENGTH: 20
<212> TYPE: DNA
<213> ORGANISM: Artificial Sequence
<220> FEATURE:
<223> OTHER INFORMATION: Forward primer for B7-H6

<400> SEQUENCE: 23
gacctggagc cattgtgtct                                               20

<210> SEQ ID NO 24
<211> LENGTH: 20
<212> TYPE: DNA
<213> ORGANISM: Artificial Sequence
<220> FEATURE:
<223> OTHER INFORMATION: Reverse primer for B7-H6

<400> SEQUENCE: 24
aagctggact gttccctgtg                                               20

<210> SEQ ID NO 25
<211> LENGTH: 19
<212> TYPE: DNA
<213> ORGANISM: Artificial Sequence
<220> FEATURE:
<223> OTHER INFORMATION: Forward primer for GADPH

<400> SEQUENCE: 25
gcaaattcca tggcaccgt                                                19

<210> SEQ ID NO 26
<211> LENGTH: 19
<212> TYPE: DNA
<213> ORGANISM: Artificial Sequence
<220> FEATURE:
<223> OTHER INFORMATION: Reverse primer for GADPH

<400> SEQUENCE: 26
tcgccccact tgattttgg                                                19
```